(12) United States Patent
Brook et al.

(10) Patent No.: US 8,168,741 B2
(45) Date of Patent: May 1, 2012

(54) CHELATING SILICON-BASED POLYMERS

(75) Inventors: Michael Brook, Ancaster (CA);
Ferdinand Gonzaga, Hamilton (CA);
Hongjian Tian, Mississauga (CA);
Howard Ketelson, Dallas, TX (US)

(73) Assignees: Joint Intellectual Property Policy of McMaster University, Hamilton, Ontario (CA); Alcon Research, Ltd., Fort Worth, TX (US)

( * ) Notice: Subject to any disclaimer, the term of this patent is extended or adjusted under 35 U.S.C. 154(b) by 584 days.

(21) Appl. No.: 11/997,840

(22) PCT Filed: Aug. 2, 2006

(86) PCT No.: PCT/CA2006/001291
§ 371 (c)(1),
(2), (4) Date: Oct. 21, 2008

(87) PCT Pub. No.: WO2007/014471
PCT Pub. Date: Feb. 8, 2007

(65) Prior Publication Data
US 2009/0118456 A1    May 7, 2009

Related U.S. Application Data

(60) Provisional application No. 60/704,434, filed on Aug. 2, 2005, provisional application No. 60/805,401, filed on Jun. 21, 2006.

(51) Int. Cl.
*C08G 77/00* (2006.01)
*C07F 7/08* (2006.01)
(52) U.S. Cl. ............................ 528/41; 977/773; 556/437
(58) Field of Classification Search .................. 510/466; 528/41; 556/437; 977/773
See application file for complete search history.

(56) References Cited

U.S. PATENT DOCUMENTS

| 5,124,466 A | 6/1992 | Azechi et al. |
| 5,447,997 A | 9/1995 | Raleigh et al. |
| 5,707,613 A | 1/1998 | Hill |
| 6,566,322 B1 | 5/2003 | Brook et al. |
| 2003/0211050 A1* | 11/2003 | Majeti et al. ............ 424/49 |

FOREIGN PATENT DOCUMENTS

| CA | 2274040 | 11/2000 |
| CA | 2309486 | 11/2000 |

OTHER PUBLICATIONS

Faraday, M., "The Bakerian Lecture: Experimental Relations of Gold (and other Metals) to Light", Phil. Trans. Roy. Soc., vol. 147, p. 145, 1857.
Hughes, M.D. et al., "Tunable Gold Catalysts for Selective Hydrocarbon Oxidation Under Mild Conditions", Nature, vol. 437, No. 7062, pp. 1132-1135, 2005.
Murphey, C. J. et al., "An Improved Synthesis of High-Aspect-Ratio Gold Nanorods", Advan. Mater. vol. 15, p. 414, 2003.
Pernodet, N. et al., "Adverse Effects of Citrate/Gold Nanoparticles on Human Dermal Fibroblasts", Small, vol. 2, No. 6, pp. 766-773, 2006.
Pileni, M., "The Role of Soft Colloidal templates in Controlling the Size and Shape of Inorganic Nanocrystals", Nature Materials, vol. 2, pp. 145-150, 2003.
Siwy, Z. et al., "Protein Biosensors Based on Biofunctionalized Conical Gold Nanotubes", J. Am. Chem. Soc., vol. 127, No. 14, pp. 5000-5001, 2005.
Stoner, E.J. et al., "Allylation of Erythromycin Derivatives: Introduction of Allyl substituents into Highly Hindered Alcohols", J. Org Chem. vol. 68, pp. 8847-8852, 2003.
Sun, S. et al., "Monodisperse FePt nanoparticles and Ferromagnetic FePt Nanocrystal Superlattices", Science, vol. 287, 1989-1992, 2000.
Thomas, J.M., "Colloidal Metals: Past, Present and Future", vol. 60, No. 10, pp. 1517-1528, 1988.
Turkevich, J., et al., "A Study of the Nucleation and Growth Processes in the Synthesis of Colloidal Gold", Disc. Faraday Soc. vol. 11, p. 55, 1951.
Wang, J. F. et al., "Highly Polarized Photoluminescence and Photodetection from Single Indium Phosphide Nanowires", Science, vol. 293, 1455-1457, 2001.

* cited by examiner

*Primary Examiner* — Ling Choi
*Assistant Examiner* — Chun-Cheng Wang
(74) *Attorney, Agent, or Firm* — Rothwell, Figg, Ernst & Manbeck, P.C.

(57) ABSTRACT

The present invention relates to novel silicon-based polymers, particularly silicon-based polymers having citrate groups, and their use as chelating agents, for forming nanostructures, as surfactants, as reducing agents and as stabilizers.

39 Claims, 10 Drawing Sheets

Method: pendant drop
PBS Buffer, pH 7.4
CMC: 0.5 mM
Surface tension (CMC) 22.4 mN/m

A  B

C

A

B

Au  Pt  Ni

1 DAY               2 DAYS              11 DAYS pH6.3 pH 7.8 pH 8.2

CHELATING SILICON-BASED POLYMERS

CROSS REFERENCE TO RELATED APPLICATION

This application is a 35 U.S.C. 371 National Phase Entry Application from PCT/CA2006/001291, filed Aug. 2, 2006 which claims the benefit of Provisional Applications Nos. 60/704,434 filed Aug. 2, 2005 and 60/805,401 filed Jun. 21, 2006, the disclosures of which are incorporated herein in their entirety by reference.

FIELD OF THE INVENTION

The present invention relates to silicon-based polymers, and in particular silicon-based polymers having citrate groups, and their use, particularly in methods for the formation of controlled morphology metal nanostructures.

BACKGROUND OF THE INVENTION

Inorganic nanocrystals exhibit size and shape-dependant physicochemical properties that can be broadly exploited as bioactive agents (Pernodet, N. et al., "Adverse Effects of Citrate/Gold Nanoparticles on Human Dermal Fibroblasts", Small, Vol. 2, No. 6, Pages 766-773, 2006), catalysts (Hughes, M. D. et al., "Tunable Gold Catalysts for Selective Hydrocarbon Oxidation Under Mild Conditions", Nature, Vol. 437, No. 7062, Pages 1132-1135, 2005), biosensors (Siwy, Z. et al., "Protein Biosensors Based on Biofunctionalized Conical Gold Nanotubes", J. Am. Chem. Soc., Vol. 127, No. 14, Pages 5000-5001, 2005), data storage (Sun, S. et al., Science, Vol. 287, 1989-1992, 2000) and optics (Wang, J. F. et al, Science, Vol. 293, 1455-1457, 2001). There is a strong interest in controlling the synthesis and morphology of metal structures on the nanoscale. Several methods for nanostructure synthesis are now available with, in some cases, control over their composition and architecture. Faraday described the formation of gold colloids nearly 150 years ago (Faraday, M., Phil. Trans. Roy. Soc., Vol. 147, Page 145, 1857). Boiling gold salts with citric acid (Turkevich, J., et al., Disc. Faraday Soc. Vol. 11, Page 55, 1951) gives primarily pyramidal particles (Thomas, J. M., "Colloidal Metals: Past, Present and Future", Vol. 60, No. 10, Pages 1517-1528, 1988). A series of different strategies including the use of surfactants, high UV and chemical vapor deposition (CVD) are being exploited in an attempt to gain more control over the preparation of metallic structures. Generic routes to a broad range of nanostructures for specific applications, using the same set of synthetic tools, have proven elusive.

There are a wide variety of applications that require control of the interfacial properties between immiscible components, such as water-in-oil emulsions or oil-in-water emulsions. Generally, to obtain good performance, it is necessary to stabilize the interface between the two immiscible components. One simple example is the use of coupling agents to modify silica surfaces so that silica may be used to reinforce organic polymers, with which it is otherwise incompatible (Plueddeman, E. P., Silane Coupling Agents, Plenum Press: New York, $2^{nd}$ Ed. 1991). Another example is the use of surfactants to stabilize oils in water, such as in cleaning and conditioning applications.

Silicones are among the most surface-active materials ("surfactants") known. They diffuse rapidly to interfaces and readily spread. Spreading of the silicone may be facilitated by the incorporation of polar groups on the silicone backbone. Some of the most effective spreading compounds, particularly at solid/liquid/air surfaces, are the so-called "superwetters" made by manufacturers including Crompton Corp. and Dow Corning. The general structure of these superwetters is $((CH_3)_3SiO)_2Si(CH_3)(CH_2)_3(OCH_2CH_2)_nOZ$, where Z may be H, $CH_3$, $CH_3COO$, etc. (Hill, R. M., Silicone Surfactants, Dekker, 1999).

Liquid-liquid interfaces are generally stabilized with silicones bearing non-ionic hydrophilic groups. Common examples include derivatives of so-called silicone polyols; that is silicones containing polyether sidechains. U.S. Pat. No. 5,707,613 issued to Hill teaches that these compounds are particularly useful at stabilizing water/silicone interfaces. Ionic silicone copolymers can also be used to stabilize such interfaces. U.S. Pat. No. 5,124,466 issued to Azechi et al. teaches that ammonium-modified silicone surfactants are useful in the stabilization of silicone emulsions in water. Anionic silicone surfactants are also known. U.S. Pat. No. 5,447,997 issued to Releigh et al. teaches silicones containing carboxylic acids whose surface properties change as a function of pH.

The surface activity of silicones, whether cationic, anionic, zwitterionic or non-ionic, cannot be readily changed, although pH modifications may affect the behavior of some types of ammonium compounds at high pH or carboxylic acids and other acids at low pH. There are advantages in being able to change the surface activity of a surface active material so as to change the properties of the system in accordance with its particular use, for example, to flocculate emulsions on demand. For example, carboxylic acids and polymers derived therefrom (e.g., CARBOPOL™ (available from BF Goodrich)) can swell in water and stabilize interfaces upon pH changes in such instances as when bases convert neutral carboxylic acids to carboxylates. In this respect, silicones having a pH sensitivity, by virtue of amine or carboxylic acid groups, are known.

The properties of ionic surfactants may not only be changed by pH, but by the nature of the counterions as well. For example, carboxylates with monovalent counterions such as sodium swell well with water. In contrast, the presence of multivalent counterions in the same system lead to ionic crosslinking and a reduction of swelling. At an interface, the surface activity of such materials is similarly affected by the nature of the counterion.

Multidentate ligands (or "chelating agents") bind metals very tightly. The classic example is EDTA (ethylenediaminetetraacetic acid). EDTA, normally in its calcium, disodium salt form, is frequently found in food products. Heavy metal ions coming into contact with the EDTA will complex with the amine and carboxylic acid groups, displacing the sodium/calcium ions. The binding efficiency of EDTA and its derivatives is known for many metals and their different oxidation states. Chelating agents are added to many different formulations for different purposes. They have also been bound to polymers. For example, chelating groups similar to those mentioned above are used as supports in affinity chromatography.

U.S. Pat. No. 6,566,322 issued to R. S. Stan and M. A. Brook describes the use of silicones capable of chelating metals. In this case, nitrilotriacetic acid derivatives were added to linear silicones either at the termini, or pendant along the chain. While these materials offer advantageous properties, there remains a need to develop materials with such properties and the additional ability to undergo redox chemistry.

SUMMARY OF THE INVENTION

It has been found that a novel class of silicon-based polymer compounds are useful for metal chelation, formation of nanostructures, as surfactants, as reducing agents and as stabilizers.

Accordingly, the present invention relates to a silicon-based polymer comprising a hydrophobic backbone and having at least one citrate-based metal binding site X defined as:

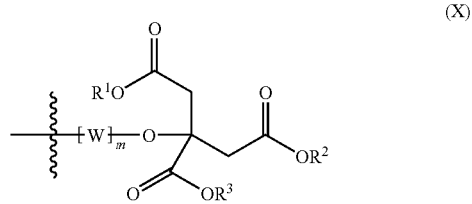

wherein
X is optionally bonded to a metal;
W is a linker group;
m is 0 or 1; and
$R^1$, $R^2$ and $R^3$ are independently selected from the group consisting of H, $C_{1-20}$alkyl, aryl, functional $C_{1-20}$alkyl and functional aryl.

In an embodiment of the present invention, the hydrophobic backbone is selected from the group consisting of a polysiloxane, polycarbosiloxane, polysilane and polycarbosilane.

The present invention also relates to a silicon-based polymer of the formula (I):

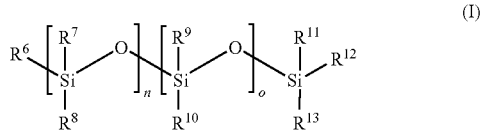

wherein at least one of $R^6$ to $R^{13}$ is a citrate-based metal binding site X defined as:

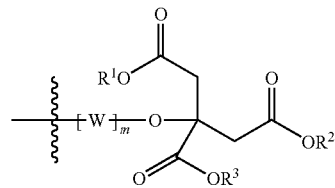

and the remaining $R^6$ to $R^{13}$ are independently selected from the group consisting of H, $C_{1-20}$alkyl, aryl, functional $C_{1-20}$alkyl and functional aryl;
X is optionally bonded to a metal;
$R^1$ to $R^3$ are independently selected from the group consisting of H, $C_{1-20}$alkyl, aryl, functional $C_{1-20}$alkyl and functional aryl;
W is a linker group;
m is 0 or 1;
n and o are each greater than or equal to 0 with the proviso that sum of n and o is greater than 0; and
with the proviso that the silicon-based polymer has a total molecular weight between about 500 and 500,000 g/mol.

An advantage of the present invention is that by using a citrate group, the silicon-based polymers of the present invention, which can be used as surfactants, can further be used to structure pre-existing nanoparticles or nanoparticles during their formation. Due to the redox potential and metal chelation properties provided by the citrate group, both water in oil and oil in water mixtures may be structured for use to control the assembly of nanoparticles of noble metals and to reduce metal ions to metals.

Polymer surfactants of the present invention have been shown to self-assemble in aqueous solutions, and more specifically aqueous solutions containing metal ions. Since citric acid contains an alcohol and three carboxylic acid groups, the carboxylic acid cluster can bind to single or multivalent metal ions, and thus facilitate the reduction of selected metal ions, for example, $Au^{3+} \rightarrow Au^0$. A further embodiment of the current invention is the presence of hydrophilic constituents on the surfactant that have the ability to reduce metal ions. Another embodiment of the invention is the presence of citric acid groups which can be bound through the alcohol group at C2 and are able to reduce selected metal ions. Accordingly, it has been found that when the polymers of the present invention were added to aqueous solutions of metal ions, the polymers self-assembled and structured the aqueous solutions, resulting in the formation of vesicles, ribbons, and other structures well known to those skilled in the art.

In a further embodiment of the present invention, once the metal ion containing solution is structured, the metal ions are reduced to metals of various structures on a nanoscale including spheres, rods, prisms, foams, leaves and plates. In a further embodiment, the resulting structure of the metal and the rate of its formation are controlled by the formulation, including the specific surfactant used, the concentration of the surfactant, the specific metal ion salt, the concentration of the metal ions, the pH of the aqueous solution, the nature of light to which the mixture is exposed (visible and UV) and the presence of any additional reducing agents, for example, $NaBH_4$.

Accordingly, the present invention further relates to the use of the silicon-based polymers of the present invention for forming nanostructures, as surfactants, as reducing agents and as stabilizers. More specifically, the nanostructures are selected from the group consisting of nanoparticles and agglomerated nanoparticles, and agglomerated micelles, reverse micelles, vesicles, sheet structures and wire structures, all containing nanoparticles.

In particular, the present invention provides a method of forming metal nanostructures comprising contacting an aqueous solution of a metal salt with a polymer of the present invention. In an embodiment, the formation and morphology of the nanostructure are controlled by adjusting the specific surfactant used, the concentration of the surfactant, the specific metal ion salt, the concentration of the metal ions, the pH of the aqueous solution, the nature of light to which the mixture is exposed (visible and UV), and the presence of any additional reducing agents, for example, $NaBH_4$.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in greater detail with reference to the following drawings in which.

DETAILED DESCRIPTION OF THE INVENTION

I. Definitions

Figure 1:
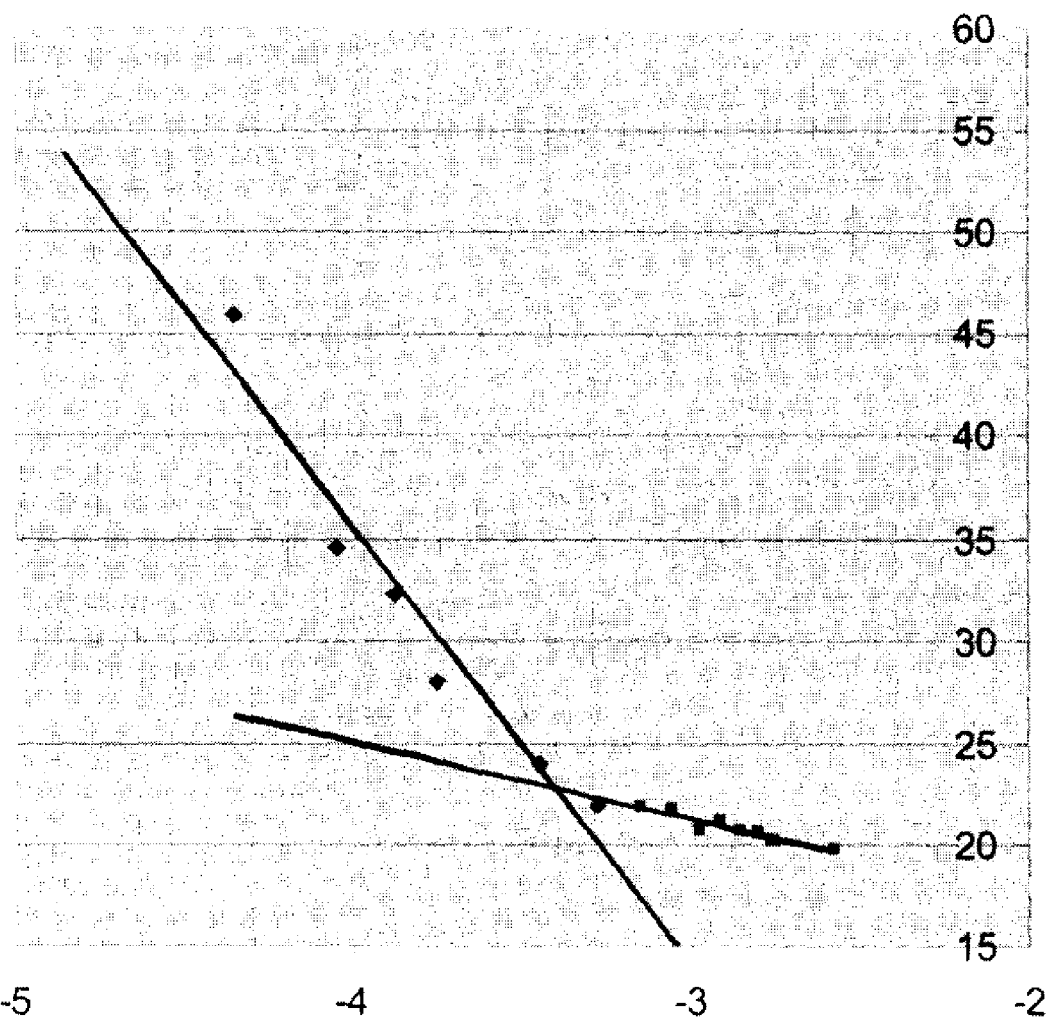
FIG. 1 shows a graph illustrating the critical micelle concentration (cmc) of Si-5.

The term "hydrophobic" as used herein means groups or molecules that would not normally be soluble in water.

The term "hydrophilic" as used herein means groups or molecules that would normally be soluble in water.

The term "alkyl" as used herein means an aliphatic hydrocarbon, linear, branched and/or cyclic having up to 20 carbon atoms.

The term "aryl" as used herein means a hydrocarbon residue base, having up to 20 carbons and containing at least one conjugated cyclic substructure, which cyclic structure may contain an O or N, and which cyclic structure may be substituted at a substitutable position with an alkyl or a fluoro group.

The term "functional alkyl" as used herein means an alkyl group having one or more functional groups selected from halogens (F, Cl, Br, I); hydroxy groups (OH); thiols (SH), sulfides (SR, where R=alkyl, functional alkyl, aryl, or functional aryl), disulfides (SSR, where R=alkyl, functional alkyl, aryl or functional aryl), alkoxy groups (RO, where R=alkyl, functional alkyl, aryl or functional aryl); primary amine ($NH_2$), secondary amine (RNR', where R and R'=alkyl, functional alkyl, aryl or functional aryl) or tertiary amino groups ($R_2N$, where R=independently, alkyl, functional alkyl, aryl or functional aryl); primary phosphino ($PH_2$), secondary phosphino (RPH, where R=alkyl, functional alkyl, aryl or functional aryl) or tertiary phosphino groups (RR'P, where R and R'=alkyl, functional alkyl, aryl or functional aryl); carboxylic acids (COOH) and their derivatives including esters (COOR, where R=alkyl, functional alkyl, aryl or functional aryl), thioesters (COSR, CSOR, where R=alkyl, functional alkyl, aryl or functional aryl) and amides ($CONH_2$, CONHR, CONRR', where R and R'=alkyl, functional alkyl, aryl or functional aryl), carbonates ($ROCO_2R'$) or derivatives such as urethanes ($OCONH_2$, OCONHR, OCONRR', NHCOOR, NR'COOR), ureas ($NHCONH_2$, $NRCONH_2$, NHCONRH, NHCONRR', NRCONHR', NRCONR'R''), where R, R' and R''=alkyl, functional alkyl, aryl or functional aryl), aldehydes (CHO), ketones (COR, where R=alkyl, functional alkyl, aryl or functional aryl), alkenes (C=C), alkynes (C≡C) and aryl.

The term "functional aryl" as used herein means an aryl group having one or more functional groups substituted at a substitutable position in which the groups are selected from halogens (F, Cl, Br, I); hydroxy groups (OH); thiols (SH), sulfides (SR, where R=alkyl, functional alkyl, aryl, or functional aryl), disulfides (SSR, where R=alkyl, functional alkyl, aryl or functional aryl), alkoxy groups (RO, where R=alkyl, functional alkyl, aryl or functional aryl); primary amine ($NH_2$), secondary amine (RNR', where R and R'=alkyl, functional alkyl, aryl or functional aryl) or tertiary amino groups ($R_2N$, where R=independently, alkyl, functional alkyl, aryl or functional aryl); primary phosphino ($PH_2$), secondary phosphino (RPH, where R=alkyl, functional alkyl, aryl or functional aryl) or tertiary phosphino groups (RR'P, where R and R'=alkyl, functional alkyl, aryl or functional aryl); carboxylic acids (COOH) and their derivatives including esters (COOR, where R=alkyl, functional alkyl, aryl or functional aryl), thioesters (COSR, CSOR, where R=alkyl, functional alkyl, aryl or functional aryl) and amides ($CONH_2$, CONHR, CONRR', where R and R'=alkyl, functional alkyl, aryl or functional aryl), carbonates ($ROCO_2R'$) or derivatives such as urethanes ($OCONH_2$, OCONHR, OCONRR', NHCOOR, NR'COOR), ureas ($NHCONH_2$, $NRCONH_2$, NHCONRH, NHCONRR', NRCONHR', NRCONR'R''), where R, R' and R''=alkyl, functional alkyl, aryl or functional aryl), aldehydes (CHO), ketones (COR, where R=alkyl, functional alkyl, aryl or functional aryl), alkenes (C=C) and alkynes (C≡C).

The term "functional alkyl groups bearing heteroatom-based ligands" as used herein means the subset of functional alkyl, having one or more O, N, or S atoms including hydroxy, thiols, sulfides, disulfides, alkoxy, primary, secondary and tertiary amino groups, primary, secondary and tertiary phosphino groups, carboxylic acids and their derivatives including esters, thioesters, amides, carbonates or their derivatives including urethanes, ureas, aldehydes and ketones.

The term "metal" as used herein means all metals of the periodic table, including without limitation, alkali metals, alkaline earth metals, transition metals, lanthanides, actinides and Group 13 elements including boron.

Those skilled in the art will appreciate that there are combinations of functional groups that will react (e.g., amines+ alkyl halides) which are thus mutually incompatible. These combinations are not to be inferred in the following discussion.

II. Compounds of the Invention

A novel class of silicon-based polymer compounds having at least one citrate-based metal binding site has been prepared. The compounds of the invention are useful as chelating agents, for formation of nanostructures, as surfactants, as reducing agents or as stabilizers.

Accordingly, the present invention relates to a silicon-based polymer comprising a hydrophobic backbone and having at least one citrate-based metal binding site X defined as:

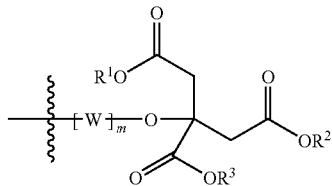
(X)

wherein
X is optionally bonded to a metal;
W is a linker group;
m is 0 or 1; and
$R^1$, $R^2$ and $R^3$ are independently selected from the group consisting of H, $C_{1-20}$alkyl, aryl, functional $C_{1-20}$alkyl and functional aryl.

Generally, the hydrophobic backbone of the silicon-based polymer is selected from the group consisting of a polysiloxane, a polycarbosiloxane, a polysilane and a polycarbosilane. More particularly, the hydrophobic nature of the silicon-based polymer is provided by organic radicals such as methyl or other alkyl groups, modified alkyl groups such as fluoroalkyl groups, aryl groups and related hydrophobic moieties, bonded to the silicon atoms in the polymer. It will be appreciated that the silicon-based polymer of the present invention includes those backbones having a "linear" structure as well as those having a "branched" structure. The terms "silicone polymer" and "polysiloxane" are used interchangeably herein.

The citrate group of the silicon-based polymer provides a tridentate metal binding site and is the hydrophilic component of the polymer. Thus, the citrate group of the silicon-based polymer may act as the chelating agent, binding to a variety of metals. The hydrophilic component may be hydrophilic prior to binding to a metal or after binding to a metal.

The metal binding sites may be covalently bonded to the silicon-based polymer backbone at one or both of the polymer's terminal ends. Alternatively, or in addition, the metal binding sites may be covalently bonded to the polymer backbone in a periodic fashion. For instance, the metal binding sites may be periodically bonded to the silicon-based polymer backbone at intervals from about every fifth to about every twentieth internal Si—O— group. It will be appreciated by those skilled in the art that the desired periodic interval between the metal binding sites will depend upon factors such as steric hindrance, polarity of the resulting silicon-based polymer and the specific demands of the application in which the silicon-based polymer are used.

The metal binding sites include a linker to covalently bond the metal binding site to the silicon-based polymer backbone. Suitable linkers and methods of their preparation are known to those skilled in the art and include those described in Brook, M. A., "Silicon in Organic, Organometallic and Polymer Chemistry" (Wiley & Sons, N.Y., 2000), which is hereby incorporated by reference in its entirety.

In an embodiment of the present invention, the linker group W is more stable to hydrolysis than the siloxane linkage in the silicon-based polymer backbone. In a further embodiment of the invention, the linker group W is selected from the group consisting of H, $C_{1-20}$alkylene, arylene, functional $C_{1-20}$alkylene and functional arylene. Particularly, W is

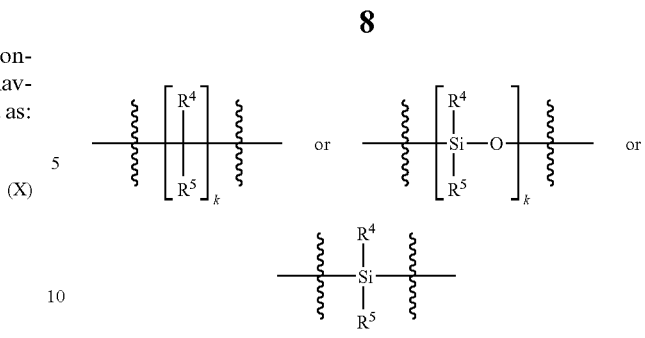

in which k is 1 to 22 and $R^4$ and $R^5$ are independently selected from the group consisting of H, $C_{1-20}$alkyl, aryl, functional $C_{1-20}$alkyl and functional aryl. Suitably, in an embodiment of the invention, k is 1 to 6 and $R^4$ and $R^5$ are independently selected from the group consisting of H, $C_{1-6}$alkyl, aryl, functional $C_{1-6}$alkyl and functional aryl. More suitably, in another embodiment, $R^4$ and $R^5$ are independently selected from the group consisting of H, $C_{1-6}$alkyl, phenyl, fluoro-substituted $C_{1-6}$alkyl and fluoro-substituted phenyl.

In an embodiment of the invention, m is 1. It is another embodiment of the invention that $R^1$, $R^2$ and $R^3$ are independently selected from the group consisting of H, $C_{1-8}$alkyl, aryl, functional $C_{1-8}$alkyl and functional aryl. Suitably, $R^1$, $R^2$ and $R^3$ are independently selected from the group consisting of H, $C_{1-6}$alkyl, phenyl, fluoro-substituted $C_{1-6}$alkyl and fluoro-substituted phenyl.

In an embodiment of the present invention, the metal which is optionally bonded to the citrate-based metal binding site is selected from the group consisting of alkali metals, alkaline earth metals, Group 13 elements, transition metals, lanthanides and actinides. In yet another embodiment of the present invention, the metal is a metal ion. More particularly, the metal ion is selected from the group consisting of $Ca^{2+}$, $Mg^{2+}$, $Ni^{2+}$, $Fe^{3+}$, $Cu^{2+}$, $Co_{2+}$, $Ag^+$, $Pt^{4+}$, $Pd^{2+}$, $Pd^{4+}$ and $Au^+$.

As will be appreciated by those skilled in the art, by having the citrate-based metal binding sites, the properties of the silicon-based polymers may be changed by modifying the pH solution, and by complexing metals of different charge states to the polymers. Under the appropriate conditions, the citrate may act to reduce the metals.

In an embodiment of the invention, the metal bonded silicon-based polymer is reduceable to form nanostructures. Particularly, in an embodiment of the invention, the morphology of the nanostructure is dependent on the silicon-based polymer. Moreover, in an embodiment of the invention, the nanostructure is selected from the group consisting of nanoparticles, agglomerated nanoparticles, agglomerated micelles and reverse micelles, vesicles, sheet structures and wire structures, the latter 5 all containing nanoparticles.

The present invention also includes within its scope a silicon-based polymer of the formula (I):

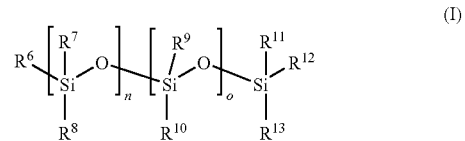
(I)

wherein at least one of $R^6$ to $R^{13}$ is a citrate-based metal binding site X defined as:

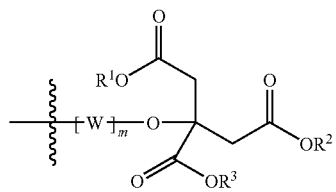

and the remaining $R^6$ to $R^{13}$ are independently selected from the group consisting of H, $C_{1-20}$alkyl, aryl, functional $C_{1-20}$alkyl and functional aryl;

X is optionally bonded to a metal;

$R^1$ to $R^3$ are independently selected from the group consisting of H, $C_{1-20}$alkyl, aryl, functional $C_{1-20}$alkyl and functional aryl;

W is a linker group;

m is 0 or 1;

n and o are each greater than or equal to 0 with the proviso that sum of n and o is greater than 0; and with the proviso that the silicon-based polymer has a total molecular weight between about 500 and 500,000 g/mol.

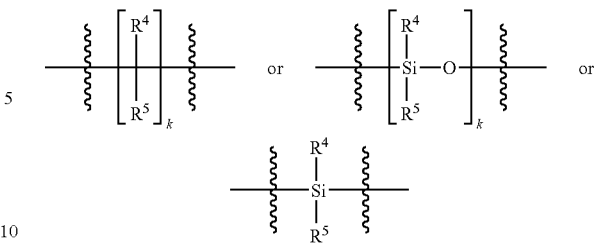

in which k is 1 to 22 and $R^4$ and $R^5$ are independently selected from the group consisting of H, $C_{1-20}$alkyl, aryl, functional $C_{1-20}$alkyl and functional aryl. It is yet another embodiment of the invention that k is 1 to 6 and $R^4$ and $R^5$ are independently selected from the group consisting of H, $C_{1-6}$alkyl, aryl, functional $C_{1-6}$alkyl and functional aryl. In another embodiment, $R^4$ and $R^5$ are independently selected from the group consisting of H, $C_{1-6}$alkyl, phenyl, fluoro-substituted $C_{1-6}$alkyl and fluorosubstitued phenyl.

In an embodiment of the invention, m is 1. In another embodiment of the invention, sum of n and o is 1 to 10. More particularly, in an embodiment of the invention, sum of n and o is 2 to 6.

The silicon-based polymer of the present invention includes the following compounds:

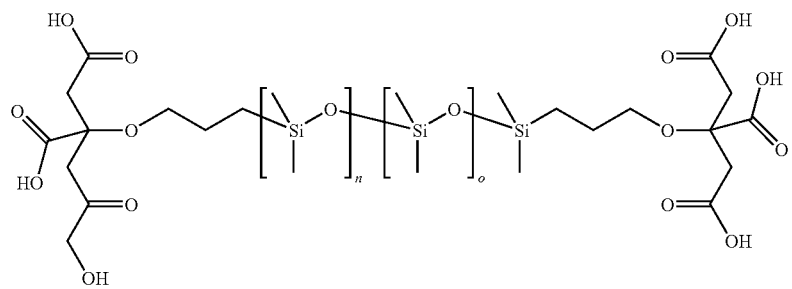

In an embodiment of the invention, the silicon-based polymer has a total molecular weight between about 500 and 15,000 g/mol. In a more particular embodiment of the invention, the silicon-based polymer has a total molecular weight between about 1500 and 15,000 g/mol.

In an embodiment of the invention, at least one of $R^6$ to $R^{13}$ is a citrate-based metal binding site X and the remaining $R^6$ to $R^{13}$ are independently selected from the group consisting of H, $C_{1-8}$alkyl, aryl, functional $C_{1-8}$alkyl and functional aryl. In another embodiment of the invention, each of $R^6$ and $R^{12}$ is a citrate-based metal binding site X. In yet another embodiment of the invention, $R^6$ is a citrate-based metal binding site X. In still another embodiment of the invention, $R^{12}$ is a citrate-based metal binding site X. Moreover, in an embodiment of the invention, $R^7$ is a citrate-based metal binding site X.

Further, in an embodiment of the invention, $R^1$ to $R^3$ are independently selected from the group consisting of H, $C_{1-8}$alkyl, aryl, functional $C_{1-8}$alkyl and functional aryl. Suitably, $R^1$ to $R^3$ are independently selected from the group consisting of H, $C_{1-6}$alkyl, phenyl, fluoro-substituted $C_{1-6}$alkyl and fluoro-substituted phenyl.

It is an embodiment of the invention that the linker group W is selected from the group consisting of H, $C_{1-20}$alkylene, arylene, functional $C_{1-20}$alkylene and functional arylene. It is another embodiment of the invention that W is in which n is 1 and in which o is greater than or equal to 0.

The silicon-based polymer of the present invention also includes the following compounds:

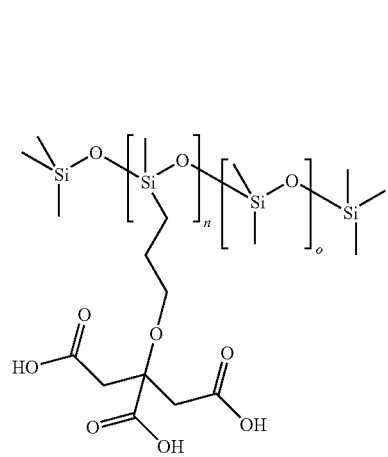

in which n is greater than or equal to 1 and in which o is greater than or equal to 0.

Further, the silicon-based polymer of the present invention includes the following specific compounds:
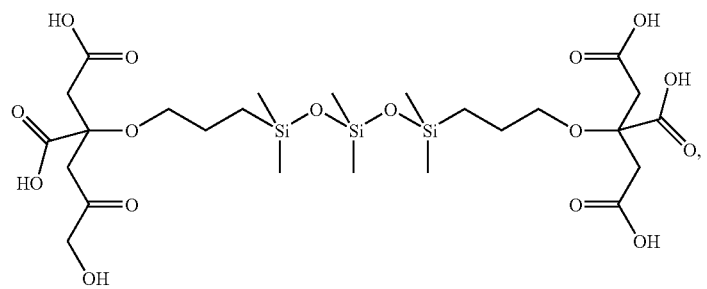 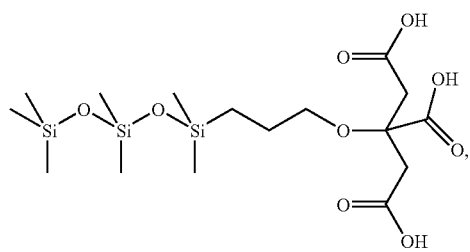
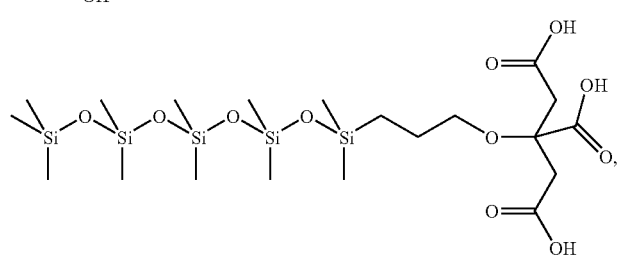
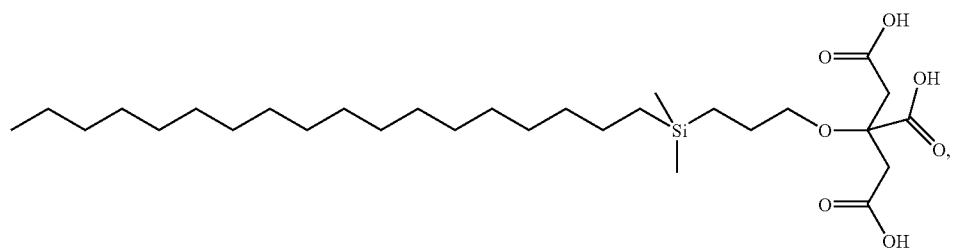
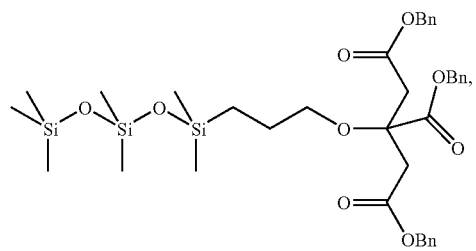 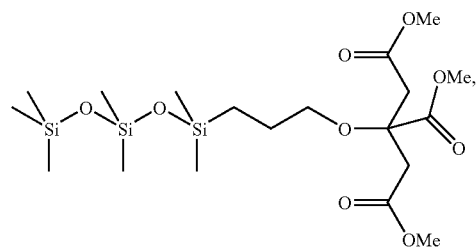
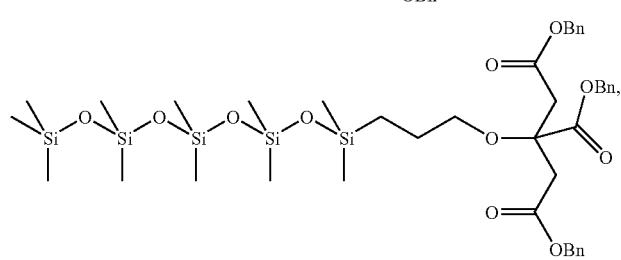
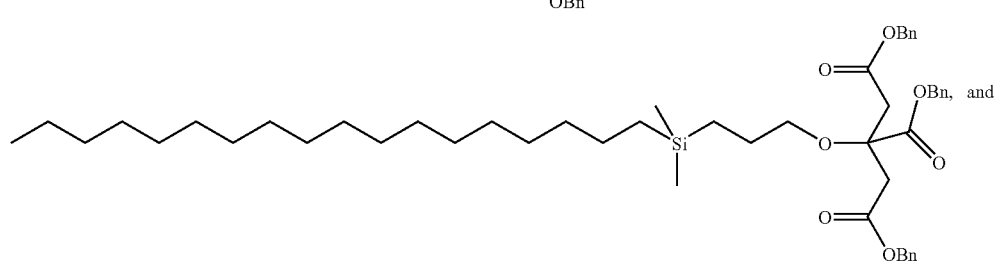

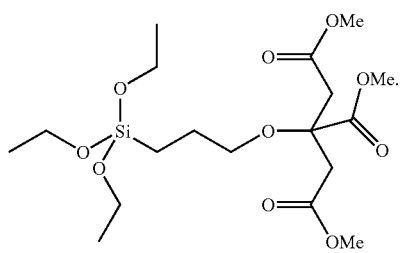

In an embodiment of the present invention, the metal is selected from the group consisting of alkali metals, alkaline earth metals, Group 13 elements, transition metals, lanthanides and actinides. In another embodiment of the present invention, the metal is a metal ion. More particularly, the metal ion is selected from the group consisting of $Ca^{2+}$, $Mg^{2+}$, $Ni^{2+}$, $Fe^{3+}$, $Cu^{2+}$, $Co^{2+}$, $Ag^+$, $Pt^{4+}$, $Pd^{2+}$, $Pd^{4+}$ and $Au^+$. Further, in an embodiment of the invention, the metal bonded silicon-based polymer is reduceable to form nanostructures. Still further, the nanostructure is of a morphology dependent by the silicon-based polymer. The nanostructure is selected from the group consisting of nanoparticles, agglomerated nanoparticles, agglomerated micelles, reverse micelles, vesicles, sheet structures and wire structures, all containing nanoparticles.

III. Preparation of the Silicon-Based Polymers of the Present Invention

As described in greater detail hereinafter, the silicon-based polymers of the present invention, functionalized with terminal and pendant citrate chelating groups, were prepared by a linear multi-step synthesis utilizing, until the last step, ester-protected carboxylic acids. This approach avoided separation steps that were difficult because of the high surface activity of both the intermediate and the final product of hydrophilically-modified silicon-based polymers. It was found that the final products and their intermediates were capable of efficiently stabilizing emulsions, as evidenced during attempted washing of reaction mixtures containing these compounds, water and either ether or chlorinated hydrocarbons.

A general scheme of the synthesis of the silicon-based polymers of the present invention from allyl-citrate is shown below:

Scheme I

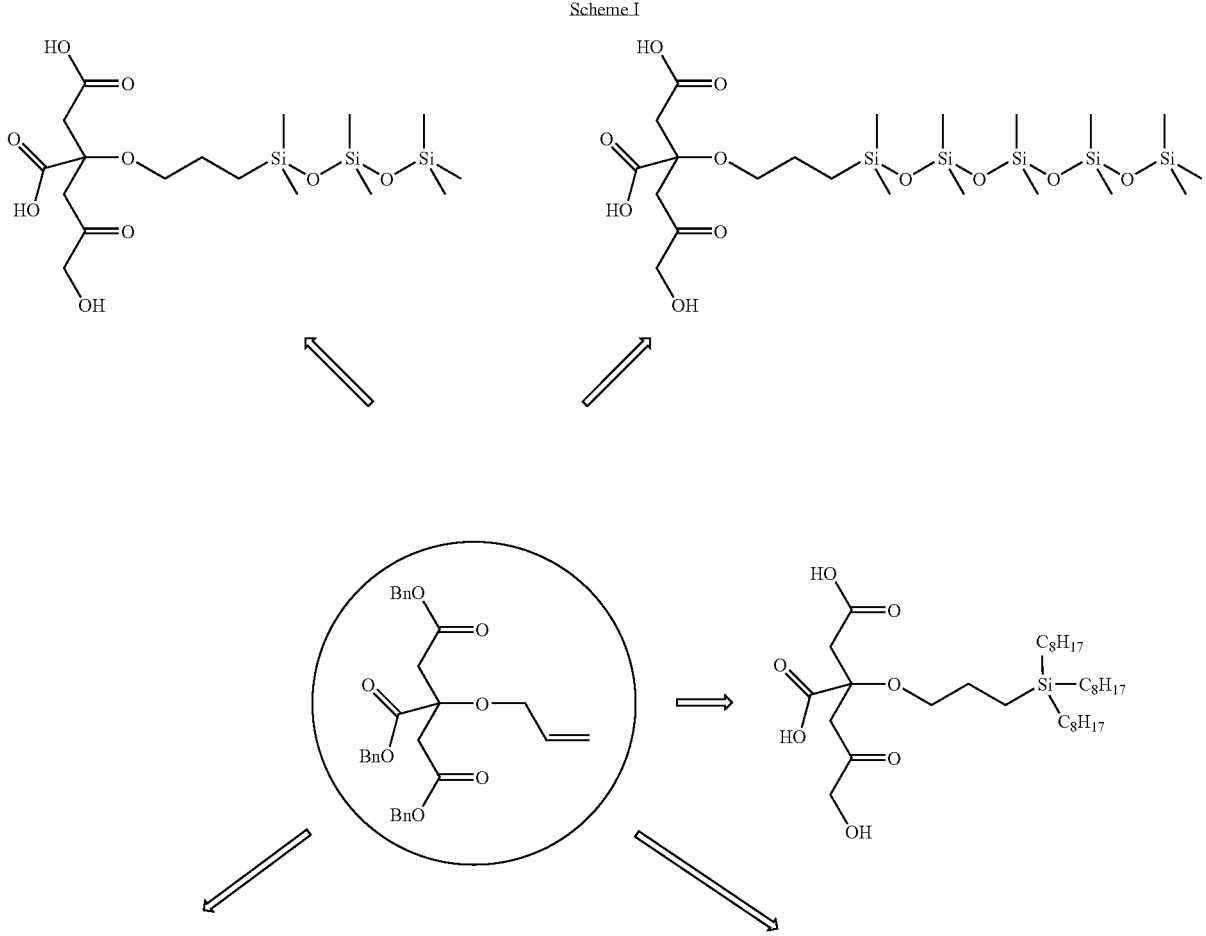

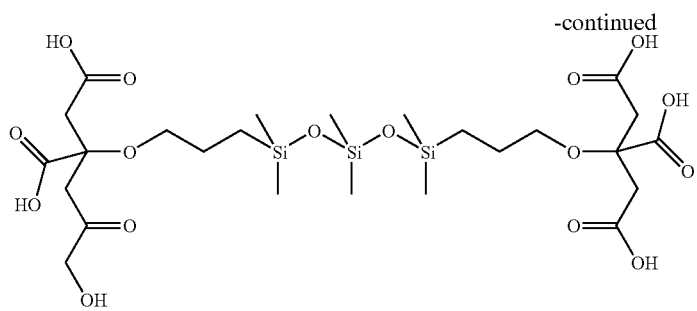
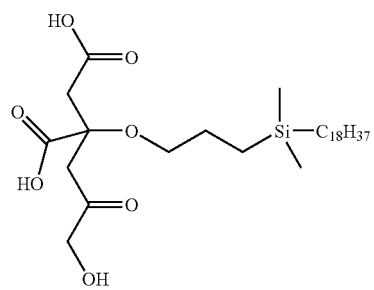

The compounds of the invention can be prepared from known starting materials using procedures known in the art.

Accordingly, the carboxylic acid groups of citric acid are first protected by suitable protecting groups, such as benzyl or methyl, to form the protected citrate, which is followed by allylic substitution reaction under catalytic condition to provide the allyl-citrate (Scheme II). Since the alcohol groups on citric acid are much less reactive than other alcohol groups, ether formation on citrates is inherently inefficient, and thus, only the formation of methyl ethers has been described in good yield. However, the present inventors have unexpectedly found that platinum catalyzed allylation provides the product in good yield.

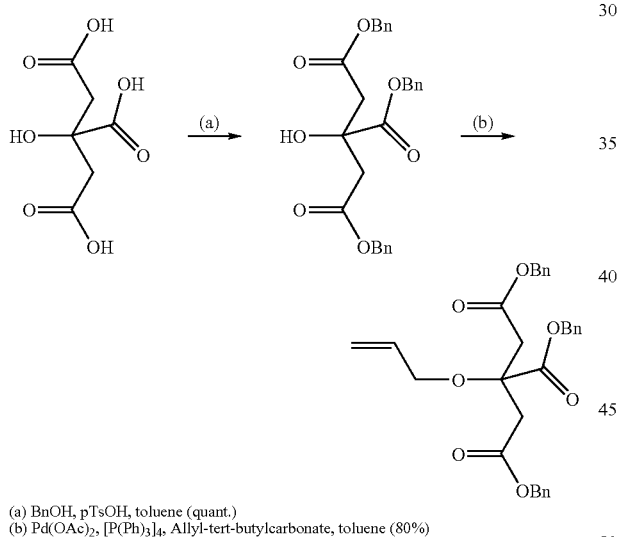

(a) BnOH, pTsOH, toluene (quant.)
(b) Pd(OAc)$_2$, [P(Ph)$_3$]$_4$, Allyl-tert-butylcarbonate, toluene (80%)

The chelating silicon-based polymers of the present invention may be synthesized from commercially available silane-containing silicones, both terminal and pendant. A general procedure is shown in Scheme III in which the allyl-citrate is first reacted with Karstedt's catalyst and hydrosilane-containing silicones. Subsequently, the protecting groups are removed by hydrolysis or hydrogenation. It will be apparent to those skilled in the art that many other silicon-based materials can similarly be prepared using analogous chemistry. Purification has been attempted on the esters, and high purity has been obtained. As such, further purification of the citrate silicones is not necessary. Although the silicon-based polymers have been found to be difficult to characterize as the free carboxylic acids, except by electrospray-mass spectroscopy, the structure of the penultimate tribenzyl esters, for instance, are easily determined by $^1$H-NMR and $^{13}$C-NMR.

Scheme III

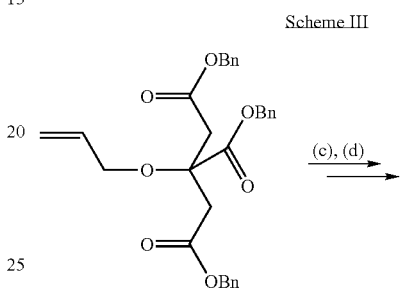

(c) Karstedt's catalyst, SiH-terminated silicone, toluene
(d) H$_2$, Pd/C, THF/MeOH (quant.)

In Scheme IV, a particular example of the synthesis of citrate-based functionalized silane polymer is shown. The allyl-citrate is first reacted with the functionalized silane and Karstedt's catalyst. Subsequently, the protecting groups are removed by hydrogenation.

Scheme IV

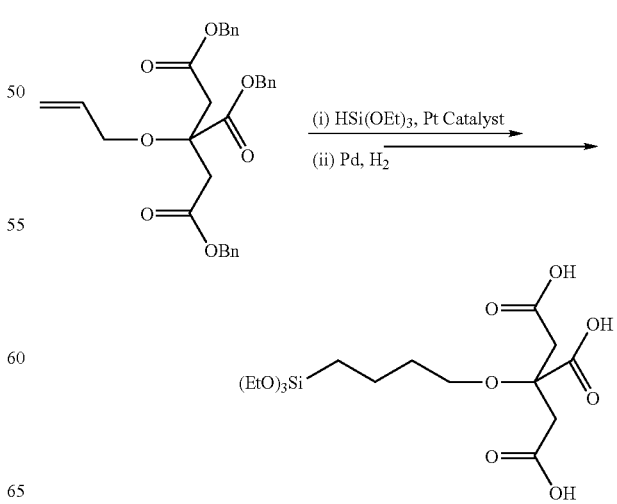

Generally, the silicone chain is connected to the citrate by a linker. The linker is initially grafted to the chelating group, that is, the citrate, and in a subsequent or concomitant step, the linker is covalently grafted to the functionalized silicone. The step of the grafting of the linker to the functionalized silicone may be carried out by hydrosilylation. As will be apparent to those skilled in the art, this step may also be catalyzed by peroxides or transition metals such as platinum. There are many convenient routes that may be utilized as well which will be readily apparent to those skilled in the art. Some, without limitation, are provided to demonstrate the flexibility of the approach.

IV: Applications of the Silicon-Based Polymers of the Present Invention

While the polymers of the present invention possess interesting surface activity in the absence of the metal, it may also undergo changes in surface activity as a function of stimuli including pH and the addition of different metals of different valencies and charges. Thus, the silicon-based polymer of the present invention has a variety of applications. The silicon-based polymers of the present invention may be used as surfactants and emulsifiers and in applications which require control of surface activity since the properties of the silicon-based polymer may be modified on demand. For example, the silicon-based polymer may be used in the stabilization of the interfaces of minerals, such as calcium carbonate, in hydrophobic media, or in the hydrophobization of such compounds for use in aqueous systems. The silicon-based polymers of the present invention may also be used in applications that require their interactions with proteins. For example, the silicon-based polymers of the present invention may be used in personal care products such as hair conditioners or hand creams. Further, they may be used in the isolation and purification of proteins by affinity chromatography, in the stabilization of proteins for delivery in washing powders or in drug delivery systems.

Figure 2:
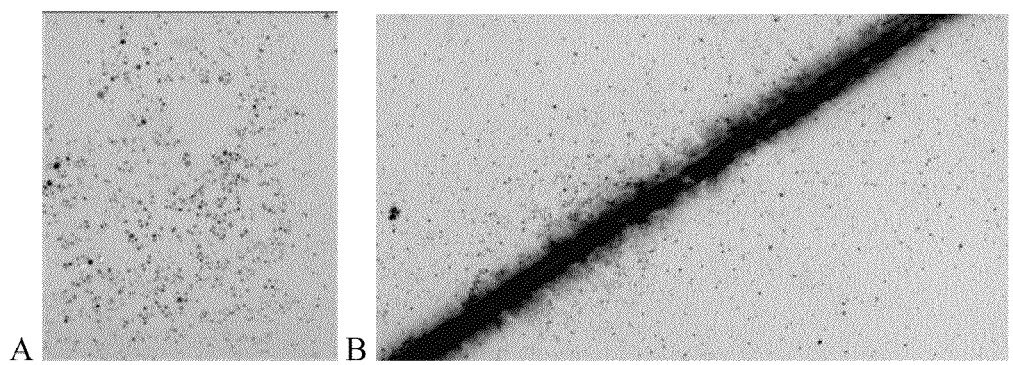
FIG. 2A shows nanoparticles obtained using $AgNO_3$ citric acid.
FIG. 2B shows nanoparticles obtained using $AgNO_3$ silicone citrate.
FIG. 2C shows the chemical structure of the Bola amphiphile.
Figure 2:
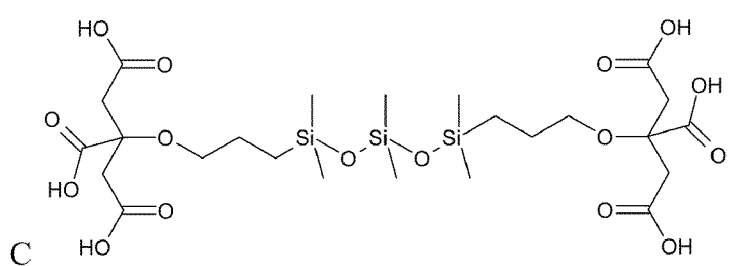
Figure 3:
FIG. 3 shows other nanoparticle morphologies obtained using an embodiment of the method of the present invention: A. Aggregated micelles; B. Rolled Sheets.
Figure 3:
Figure 3:
Figure 3:
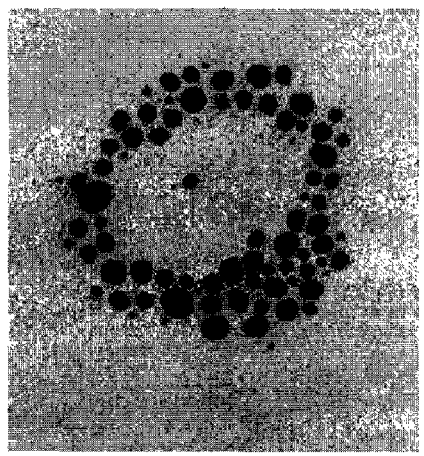

Moreover, the silicon-based polymer of the present invention may be used to form nanostructures, particularly metal nanostructures. In the classical method, colloidal particles of gold, platinum, silver and related noble metals were prepared using citrate (Turkevich, J. et al., Disc. Faraday Soc., Vol. 11, Page 55, 1951). Typically, monovalent salts were exposed to citric acid which were subsequently reduced by UV light or chemical reducing agents to the zero valent metal. A disadvantage of the classical method is that by direct reduction of the ionic solution with citrate, small nanoparticles resulted (FIG. 2A). However, under similar reaction conditions, in the case of the citrate-based silicon polymers of the present invention, such as the bola amphiphile, metal wires were observed (FIG. 2B). Thus, the surfactant character of the polymers of the present invention allows preorganization of the metal ions and constrains their subsequent assembly to provide long term organization. Accordingly, with the appropriate choice of surfactants and assembly conditions, many other morphologies are available, including aggregated micelles and "rolled sheets" (FIG. 3).

Thus, also within the scope of the present invention is the use of the silicon-based polymers of the present invention for forming nanostructures, as surfactants, as reducing agents and as stabilizers. More specifically, the nanostructures are selected from the group consisting of nanoparticles and agglomerated nanoparticles, agglomerated micelles, reverse micelles, vesicles, sheet structures and wire structures, all containing nanoparticles.

It has been unexpectedly found that, in the presence of gold cations, polymers of the present invention can induce nucleation and direct crystal growth to yield large and ultrathin gold nanostructures. The process, both pH and light dependent, presents strong analogies with the chemistry of natural iron siderophores, which can stabilize and control the photoreduction of iron cations through their complexation. The synergy between small reactive molecules leading to soft-matter assemblies and the chemistry of inorganic species can lead to morphological control of metal nanostructures in a process analogous to biomineralization. Accordingly, the flexibility in the synthesis of citric acid-based surfactants, their ability to complex several inorganic cations and their ease of self-assembly make these citric acid-based surfactants desirable for the synthesis of a wide range of inorganic nanocrystals.

Figure 4:
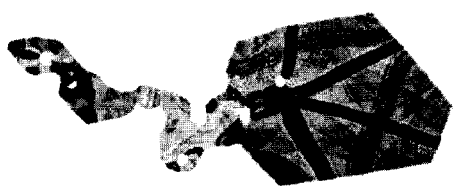
FIG. 4 shows Transmission Electron Microscopy (TEM) and Scanning Electron Microscopy (SEM) of the as synthesized product prepared by simply mixing equimolar amounts of an aqueous solution of the bola amphiphile of Example 7(iv) (pH=7.80) with a gold salt solution (sodium tetrachloroaurate, $NaAuCl_4$) at room temperature and under bench top conditions.
Figure 4:
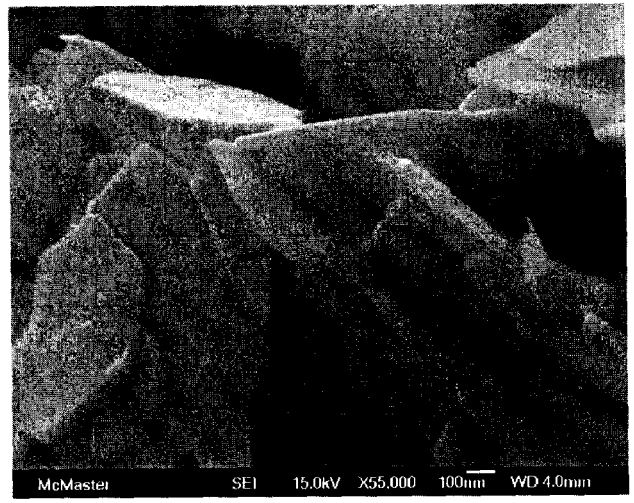

By simply mixing equimolar amounts of an aqueous solution of the amphiphile of Example 7(iv) (Bola, pH=7.80), which is described hereinafter in greater detail, with a gold salt solution (sodium tetrachloroaurate, $NaAuCl_4$) at room temperature and under bench top conditions, a controlled reduction process occurred, yielding large gold platelets of various morphologies, as can be seen by the Transmission Electron Microscopy (TEM) of the as synthesized product (FIG. 4). After 26 hours, the product was observed to be dominated by large nanoplatelets with edge lengths of several hundreds of nanometers, either with geometric shapes (hexagons, triangles, truncated triangles, all with sharp edges), or with fluidic, round and interconnected shapes. Interestingly, most of the crystals exhibited both geometrical and complex shapes. Moreover, the nanocrystals were found to be decorated with complex patterns on their surface. While not wishing to be limited by theory, this is believed to arise from the buckling and folding of their extremely thin structure. As can be seen from the Scanning Electron Microscopy (SEM, FIG. 4), these crystals appeared to have nearly exclusively flat surfaces, as indicated from their low and uniform contrast, but of different thicknesses. This result thus confirmed the previously described morphologies from TEM and also indicated that a marginal amount of highly facetted gold particles were produced. At low magnification, the crystals appeared as loose or more compact aggregates while at higher magnifications, their layered-like surface was revealed. Although typical thicknesses in the range of 20 to 30 nm were obtained from the SEM analysis, some materials were prepared with thicknesses outside this range.

To further investigate the nature of the gold nanoplatelets, High Resolution Transmission Electronic Microscopy (HR-TEM) was performed on the same samples. As can be seen from the HRTEM (FIG. 5), the well-resolved crystal lattice fringes were continuous even for the crystal contours. The observed fringe spacing of 0.257 nm agreed well with three times the $\{422\}$ lattice spacing (or $3\times\{422\}$ superlattice) of Au crystal (0.249 nm). This observation was expected for thin films or platelets with $\{111\}$ surfaces in the perpendicular direction. The corresponding Selected Area Electron Diffraction Pattern confirmed the crystallinity of the gold platelets. The diffraction peak at ~38.2° assigned to the $\{111\}$ facets of a face-centered cubic metal gold structures was high while diffraction peaks of four other facets were much weaker. It is worth noting that the intensity ratio between the $\{200\}$ and the $\{100\}$ peaks was much lower than the standard value, indicating that the gold nanoplates were primarily bound by $\{111\}$ facets, and that the basal plane, i.e., the top crystal plane plan of the nanoplates, was the $\{111\}$ plane.

While not wishing to be limited by theory, it is believed that the lipid acts as a capping agent for the growing gold crystal face. As can be seen from the HRTEM of FIG. 5, the amphiphile of Example 7(iv) was observed as a diffuse layer of irregular thickness, from <1 to >5 nm, spanning all over the surface of the gold crystals. Since the Energy Dispersive X-Ray Spectroscopy (EDS) only showed the presence of strong peaks for elemental silicon and gold, the elemental nature of this layer was confirmed.

Although previous reports in the literature have described the synthesis of two-dimensional gold nanocrystals, either through chemical, photochemical, or bioinspired processes, several aspects of the present findings are unprecedented. First of all, it has been demonstrated that a single surfactant can induce nucleation and direct anisotropic crystal growth even at low concentrations. Although surfactants have been widely used to direct crystal growth, an external reducing agent is generally needed and the surfactant is used at high concentration. This is specially true for the spherical to rod transition (Murphey, C. J. et al. Advan. Mater. Vol. 15, Page 414, 2003). Moreover, a seed mediated process is required to generate such anisotropic structures. In many cases, the inclusion of citric acid or sodium citrate is also necessary to achieve anisotropic growth, indicating that a specific interaction is involved between metal cations and citrate units during the reduction process. Another fundamental difference between the present invention and the prior art is the nature of the initiation and processing of the metal. Citric acid or sodium citrate have been widely used to reduce metal salts and stabilize noble metal nanoparticles but the method requires strong thermal or UV-photochemical activation. For example, spherical gold nanoparticles, 13 nm in size, are produced when aqueous gold salts solution are boiled for 30 minutes in the presence of citric acid ("Turkevitch" gold sols). Although the silicone citrates appear to modify the evolution of metallic structures under vigorous conditions, they can also mediate the reduction process smoothly under mild conditions including ambient temperature.

Last but not least, it is generally accepted that, although surfactants can aggregate over a wide range of morphologies, these morphologies are not retained during the reduction process (Pileni, M., "The Role of Soft Colloidal templates in Controlling the Size and Shape of Inorganic Nanocrystals", Nature Materials, Vol. 2, Pages 145-150, 2003). For example, the inorganic nanocrystals are not a replicate of the soft template in which they have been produced. The presence of round, fluid-like shapes in the present reduction process seems to indicate that, to some extent, a surfactant soft template can be converted into a rigid metal-organic ultrathin composite.

In particular, the present invention provides a method of forming metal nanostructures comprising contacting an aqueous solution of a metal salt with a polymer surfactant of the present invention. In an embodiment, the formation of the nanostructure is controlled by adjusting the specific surfactant used, the concentration of the surfactant, the specific metal ion salt, the concentration of the metal ions, the pH of the aqueous solution, the nature of light to which the mixture is exposed (visible and UV), and the optional presence of any additional reducing agents, for example, $NaBH_4$.

In an embodiment of the present invention, the metal nanostructure is a series of 2D connected wires. In a further embodiment of the invention, the metal nanostructure is a series of 3D agglomerated, connected wires resembling a foam. In yet another embodiment of the present invention, the metal nanostructures are thin, flat crystalline Au plates. In another embodiment of the present invention, the metal nanostructure is a leafy fractal structure.

It is an embodiment of the present invention where, in the method leading to metal nanostructures, an external reducing agent reduces the metal ion. In this embodiment, the product is a series of 3D agglomerated, connected wires resembling a foam. In a further embodiment, the reducing agent is comprised of a water soluble or water dispersible reducing agent, for example, $NaBH_4$ and related water dispersible or soluble boranes.

It is another embodiment of the present invention, where, in the method leading to a metal nanostructure, the polymer surfactant of the present invention reduces the metal ion to a metal. In a further embodiment of this aspect of the present invention, the rate of the reduction is mediated by visible light and the visible light leads through metal nanostructure transitions from small wires to fractal leafy structures to broad thin plates, although not exclusively. It is an embodiment of this aspect of the present invention that, the rate of the reduction is increased by UV light and the UV light leads to multiple metal nanostructure types and rapid reduction. It is an embodiment of this aspect of the present invention that the morphology of the metal nanostructure is moderated by pH. It is an embodiment of this aspect of the present invention that the surfactant resides at the metal nanomaterial surface. It is an embodiment of this aspect of the present invention that the rate of the reduction is mediated by pH.

These examples of uses are intended only to be illustrative, and not limiting. Persons skilled in the art will readily understand and appreciate a wide range of useful applications for the silicon-based polymers of the present invention.

The following non-limiting examples are illustrative of the invention:

EXAMPLES

Experimental Procedures

All syntheses were carried out in dry apparatus under a dry nitrogen atmosphere utilizing conventional bench-top techniques.

Chemical Reagents:

Citric acid (99.5+%, Aldrich), benzyl alcohol (Certified, Fisher Scientific), p-toluenesulphonic acid monohydrate (98.5+%, Aldrich), palladium acetate (99.98%, Aldrich), triphenylphosphine (99%, Aldrich), 1,1,3,3,5,5-hexamethyltrisiloxane (95%, Gelest), platinum-divinyl-tetramethyldisiloxane complex (Karstedt's catalyst) in xylene (Gelest), palladium on activated charcoal (Degussa type E101NE/W, wet/Pd 10% dry weight basis, water 50%, Aldrich), Celite (Aldrich), were used as received. Allyl-tert-butyl carbonate was prepared as described in Stoner, E. J. et al., J. Org. Chem. Vol. 68, Pages 8847-8852, 2003. Solvents were dried over activated alumina. NMR solvents ($CDCl_3$, $CD_3COCD_3$, and $CD_3OD$) were obtained from Cambridge Isotope Laboratories. De-ionized water (Millipore grade) was use for all experiments.

Spectroscopic Characterization:

$^1H$ NMR Fourier spectra were recorded on a Bruker AC-200 (200 MHz) spectrometer. Chemical shifts for $^1H$ NMR spectra are reported with respect to the following standards: residual chloroform set at 7.24 ppm, $CD_2HOD$ set at 3.30 ppm and tetramethylsilane set at 0 ppm. J-modulated $^{13}C$ NMR were recorded on a Bruker AC-200 (at 50.3 MHz for carbon). $^{13}C$ NMR spectra are reported with respect to the following standards: chloroform set at 77 ppm and tetramethylsilane set at 0 ppm. Coupling constants (J) are reported in Hertz (Hz). The abbreviations s=singlet, d=doublet, t=triplet, dd=doublet of doublets, m=multiplet, are used in reporting the spectra.

Mass spectrometry by chemical ionization (CI), with ammonia as the reagent gas ($NH_3$—CI), and electron impact (EI) mass spectra were recorded on a VG Analytical ZAB-E double focusing mass spectrometer. Low-resolution spectra were recorded for routine sample analysis of non-polar samples where appropriate. Typical experimental conditions were: mass resolution 1000, electron energy 70 eV, source temperature 200° C., source pressure of $2 \times 10^{-6}$ mbar for EI and $4 \times 10^{-5}$ mbar for CI. Mass spectra are reported as percent intensity (%) versus mass/charge (m/z) ratio.

Pneumatically-assisted electrospray ionization mass spectrometry ESMS was performed on a Micromass Quattro-LC triple quadrupole mass spectrometer with dichloromethane, dichloromethane:methanol (50/50) or methanol as the mobile phase at a flow rate of 15 μL/min, with use of a Brownlee Microgradient syringe pump. Samples were dissolved in dichloromethane:methanol (50/50) or pure methanol. Ammonia or $NH_4OAc$ was added for analysis in the negative mode; for analysis in the positive mode, formic acid was added. Mass spectra are reported as percent intensity (%) versus mass/charge (m/z) ratio.

Example 1

Preparation of 3-benzyloxycarbonyl-3-(triethoxysilylpropyloxy)-pentanedioic acid dimethyl ester (i) Preparation of 3-hydroxy-pentanedioic acid dibenzyl 3-benzyloxycarbonyl ester

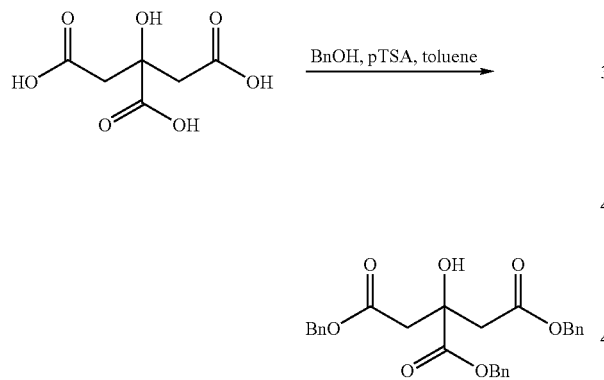

Citric acid (9.00 g, 46.8 mmol), benzyl alcohol (15.4 mL, 128.0 mmol) and toluene were placed in a 250 mL round-bottom flask. A catalytic amount of pTSA (0.10 g) was added and the reaction mixture was then stirred and refluxed with azeotropic removal of the water produced during the ester formation (Dean-Stark). After 18 hours, the mixture was allowed to cool to room temperature. The solvent and unreacted benzyl alcohol were removed in vacuo. The residue was dissolved in EtOAc and washed twice with saturated aqueous $NaHCO_3$, twice with water, and finally twice with brine. The organic phase was dried over $Na_2SO_4$ and the solvent was removed under reduced pressure, leaving an oily substance which subsequently crystallized slowly at room temperature. Recrystallization in Hexanes/EtOAc (95:5) afforded 21.6 g (quantitative) of the title compound as a white solid. $^1$H NMR (Acetone-d6, 200 MHz): δ 2.83 (br.s, 1H); 2.97 (dd, 4H, $J^1$=15.5 Hz, $J^2$=28.9 Hz); 5.07 (s, 6H); 7.30-7.35 (m, 15H). $^{13}$C NMR (Acetone-d6, 200 MHz): δ 43.89; 66.70; 67.76; 74.16; 128.83; 129.11; 136.53; 136.88; 169.96; 173.52. MS: ES-positive mode: (m/z): 463.3 (M+H$^+$) (calculated: M=462.50). 480.4 (M+NH$_4^+$), 485.3 (M+Na$^+$).

(ii) Preparation of 3-allyloxy-3-benzyloxycarbonyl-pentanedioic acid dibenzyl ester

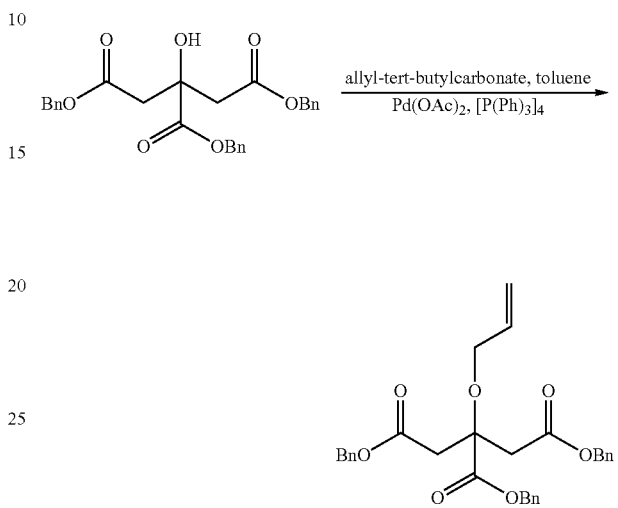

Under a nitrogen atmosphere, 3-hydroxy-pentanedioic acid dibenzyl 3-benzyloxycarbonyl ester (10.32 g, 22.3 mmol) was introduced in a round-bottom flask, followed by allyl-tert-butyl-carbonate (5.29 g, 33.5 mmol) and 110 mL of dry toluene. Palladium acetate (30 mg, 0.13 mmol) and triphenylphosphine (0.31 g, 1.18 mmol) were then added and the mixture was refluxed overnight. After being cooled to room temperature, the reaction medium was washed with dilute aqueous $NaHCO_3$, water, then brine. The organic phase was dried over $Na_2SO_4$ and the volatiles were removed in vacuo. The residue was purified by chromatography over a silica gel column, eluting with increasing amounts of EtOAc in Hexanes (9:1 to 4:1) to afford 8.97 g of the title compound (80%) as a clear oil. $^1$H NMR (Acetone-d6, 200 MHz): δ 3.19 (dd, 4H, $J^1$=15.7 Hz, $J^2$=32.7 Hz); 4.03 (d, 2H, J=5.2 Hz); 4.90-5.20 (m, 8H); 5.60-5.90 (m, 1H); 7.34 (br.s, 15H). $^{13}$C NMR (Acetone-d6, 200 MHz): δ 39.86; 66.20; 66.73; 67.58; 79.21; 116.36; 128.78; 128.83; 129.15; 135.24; 136,55; 136.89; 169.91; 170.64. MS: ES-positive mode: (m/z) 503.4 (M+H$^+$), calculated: M=502.57; 520.4 (M+NH$_4^+$), 525.3 (M+Na$^+$).

(iii) Preparation of 3-benzyloxycarbonyl-3-(triethoxysilylpropyloxy)-pentanedioic acid dimethyl ester

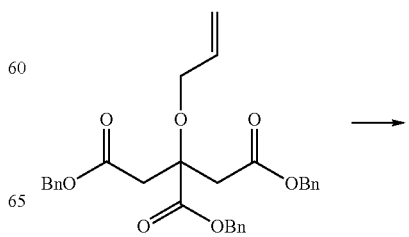

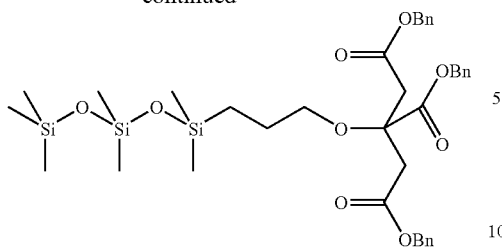

In a round-bottom flask, 3-allyloxy-3-benzyloxycarbonyl-pentanedioic acid dibenzyl ester (5.03 g, 10 mmol) in 25 mL of dry toluene was introduced, followed by heptamethyltrisiloxane (3.34 g, 15 mmol). Hydrosilylation catalyst, platinum-divinyltetramethyldisiloxane complex in xylenes solution (0.02 mL), was added and the mixture was stirred at room temperature in a dry atmosphere for 15 hours. The volatiles were then removed in vacuo without heating and the residue was purified by chromatography over a silica gel column, eluting with Hexanes/Ethyl acetate (25:1 to 4:1) to afford 6.45 g (89%) of the title compound as a colorless oil. $^1$H NMR (CDCl$_3$, 200 MHz): δ 0.02 (s, 6H); 0.05 (s, 6H); 0.09 (s, 9H); 0.37 (m, 2H); 1.47 (m, 2H); 3.18 (dd, 4H, J$^1$=15.7 Hz, J$^2$=32.9 Hz); 3.34 (t, 2H, J=6.8 Hz); 5.08 (s, 4H); 5.12 (s, 2H); 7.32 (br.s, 15H). $^{13}$C NMR (CDCl$_3$, 200 MHz): δ 0.82; 2.03; 2.57; 14.68; 24.32; 39.82; 67.18; 67.99; 68.16; 77.13; 128.95; 129.11; 129.25; 136.06; 136.35; 170.43; 171.20. MS: ES-positive mode: (m/z) 725.3 (M+H$^+$), calculated: M$^+$=725.08.

Example 2

Preparation of 3-methoxycarbonyl-3-(triethoxysilyl-propyloxy)-pentanedioic acid dimethyl ester

(i) Preparation of 3-hydroxy-3-methoxycarbonyl-pentanedioic acid dimethyl ester

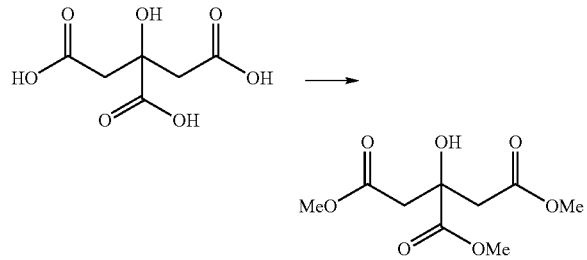

To a stirred solution of citric acid (9.00 g, 46.8 mmol) in absolute methanol at 0° C. under a nitrogen atmosphere, thionyl chloride (20.50 mL, 0.28 mol) was carefully added. The reaction mixture was stirred at 0° C. for an hour then at room temperature overnight. The volatiles were then removed in vacuo. The residual solid was recrystallized from hexane/ethylacetate to yield 10.80 g (98%) of the title compound as white crystals. $^1$H NMR (Acetone-d6, 200 MHz): δ 2.85 (dd, 4H, J$^1$=15.4 Hz, J$^2$=27.2 Hz); 3.60 (s, 6H); 3.72 (s, 3H); 4.50 (br.s, 1H). $^{13}$C NMR (Acetone-d6, 200 MHz): δ 43.60; 51.73; 52.74; 73.97; 170.55; 174.12. MS: ES-positive mode (m/z): 235.1 (M+H$^+$), calculated: M$^+$=234.21.

(ii) Preparation of 3-allyloxy-3-methoxycarbonyl-pentanedioic acid dimethyl ester

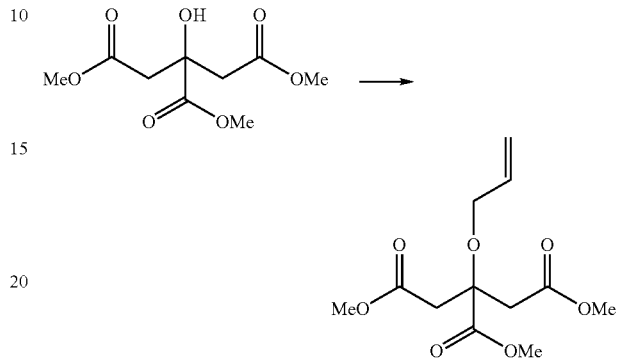

3-Allyloxy-3-methoxycarbonyl-pentanedioic acid dimethyl ester was prepared in a 91% yield using the same protocol as in Example 1(ii). The reaction time was shortened to 4 hours. $^1$H NMR (CDCl$_3$, 200 MHz): δ 3.10 (dd, 4H, J$^1$=15.7 Hz, J$^2$=35.5 Hz); 3.67 (s, 6H); 3.77 (s, 3H); 4.02 (d, 2H, J=5.3 Hz); 5.14 to 5.27 (m, 2H); 5.70 to 5.90 (m, 1H). $^{13}$C NMR (CDCl$_3$, 200 MHz): δ 39.79; 52.59; 53.34; 66.55; 79.15; 117.58; 134.61; 170.92; 171.80. MS: (m/z) ES-positive mode: 275.3 (M+H$^+$), calculated: M$^+$=274.27.

(iii) Preparation of 3-methoxycarbonyl-3-(triethoxysilylpropyloxy)-pentanedioic acid dimethyl ester

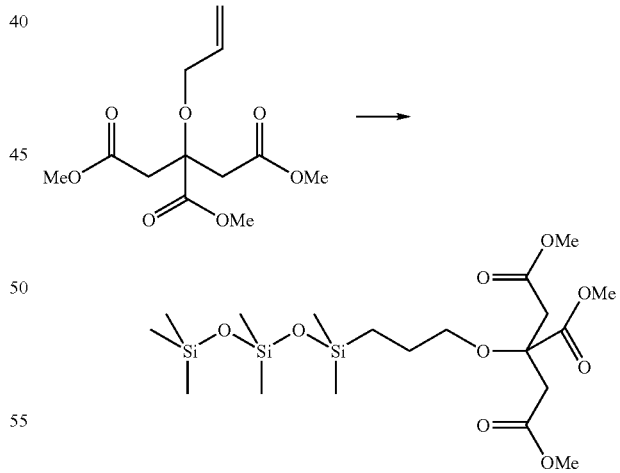

In a round-bottom flask, 3-allyloxy-3-methoxycarbonyl-pentanedioic acid dimethyl ester (2.74 g, 10 mmol) was introduced in 25 mL of dry toluene, followed by triethoxysilane (2.63 g, 16 mmol). Hydrosilylation catalyst, platinum-divinyltetramethyldisiloxane complex in xylenes solution (0.02 mL), was added and the mixture was stirred at 80° C. in a dry atmosphere for 16 hours. The volatiles were then removed in vacuo. The residue was dissolved in dry dichloromethane, a spatula of activated carbon was added, and the mixture was stirred for 3 hours under nitrogen. The mixture was then filtered over a 0.45 μm Teflon filter and the solution was evaporated to dryness to yield the title compound (3.75 g, 86%) as an oil that was used without further purification.

Example 3

Preparation of Si-5-benzyl ester

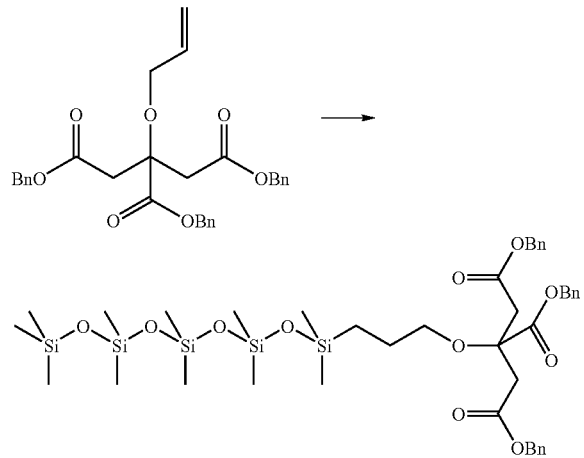

The general procedure in Example 1(iii) was followed. The characterization data for Si-5-benzyl ester is as follows. $^1$H NMR (CDCl$_3$, 200 MHz): δ 0.05 (m, 33H); 0.37 (m, 2H); 1.43 (m, 2H); 3.16 (dd, 4H, J$^1$=15.7 Hz, J$^2$=33.6 Hz); 3.35 (t, 2H, J=6.9 Hz); 5.06 (s, 4H); 5.10 (s, 2H); 7.31 (br.s, 15H). $^{13}$C NMR (CDCl$_3$, 200 MHz): δ 0.82; 1.93; 2.56; 14.66; 24.31; 39.82; 67.17; 67.99; 68.15; 79.11; 128.95; 129.12; 129.25; 136.06; 136.35; 170.43; 171.19. MS: ES-positive mode: (m/z): 890.7 (M+NH$_4^+$), calculated: M=873.39.

Example 4

Preparation of Si—C18-benzyl ester

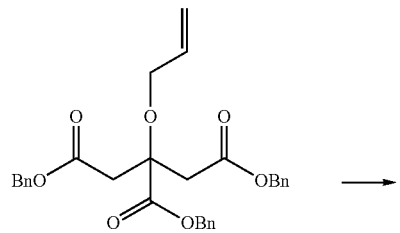

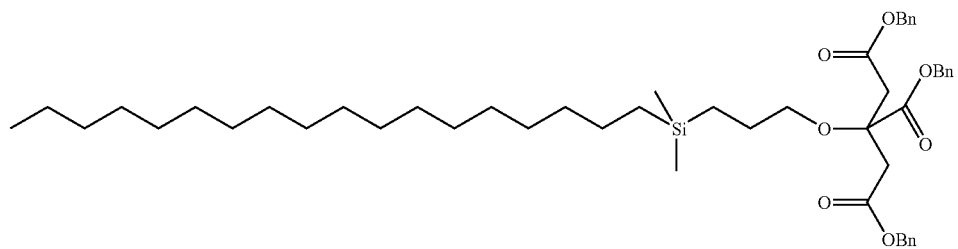

The general procedure in Example 1 (iii) was followed. The characterization data for Si—C18-benzyl ester is as follows. $^1$H NMR (CDCl$_3$, 200 MHz): δ −0.10 (s, 6H); 0.29 (m, 2H); 0.43 (m, 2H); 0.88 (t, 2H, J=6.5 Hz); 1.25 (br.s, 32H); 1.40 (m, 2H); 3.16 (dd, 4H, J$^1$=15.7 Hz, J$^2$=33.8 Hz); 3.30 (t, 2H, J=6.8 Hz); 5.07 (s, 4H); 5.10 (s, 2H); 7.31 (br.s, 15H). $^{13}$C NMR (CDCl$_3$, 200 MHz): δ −2.77; 11.61; 14.87; 15.86; 23.43; 24.59; 24.95; 30.16; 30.44; 32.66; 34.49; 39.86; 67.18; 67.98; 68.38; 79.10; 128.94; 129.12; 129.23; 136.03; 136.33; 170.42; 171.22.

Example 5

Preparation of Bola Benzyl Ester

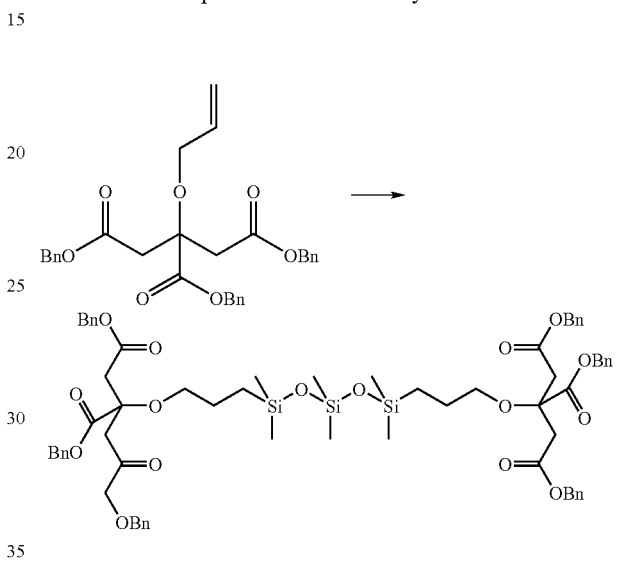

In a round bottom flask, 3-allyloxy-3-benzyloxycarbonyl-pentanedioic acid dibenzyl ester (5.03 g, 10 mmol) in 25 mL of dry toluene was introduced, followed by 1,1,3,3,5,5-hexamethyltrisiloxane (4.38 g, 21 mmol) in dry toluene (10 mL). Karstedt's platinum hydrosilylation catalyst, platinum-divinyltetramethyldisiloxane complex in xylenes solution (0.02 mL) was added and the mixture was stirred at room temperature in a dry atmosphere for 24 hours. The volatiles were then removed in vacuo without heating, and the residue was purified by chromatography over a silica gel column, eluting with hexanes/ethyl acetate (15:1 to 4:1) to afford 10.14 g (84%) of the title compound as a colorless viscous oil. $^1$H NMR (CDCl$_3$, 200 MHz): δ −0.01 (s, 6H); 0.02 (s, 12H); 0.37 (m, 4H); 1.44 (m, 4H); 3.17 (dd, 8H, J$^1$=15.7 Hz, J$^2$=32.2 Hz); 3.33 (t, 4H, J=6.9 Hz); 5.06 (s, 8H); 5.10 (s, 4H); 7.31 (br.s, 30H). $^{13}$C NMR (CDCl$_3$, 200 MHz): δ 0.85; 2.07; 14.66; 24.31; 39.83; 67.18; 67.99; 68.13; 79.10; 128.96; 129.12; 129.25; 136.05; 136.34; 170.42; 171.19. MS: ES-positive mode: (m/z) 1213.6 (M+H$^+$), calculated: M$^+$=1213.62.

Example 6

Preparation of SI-Coup

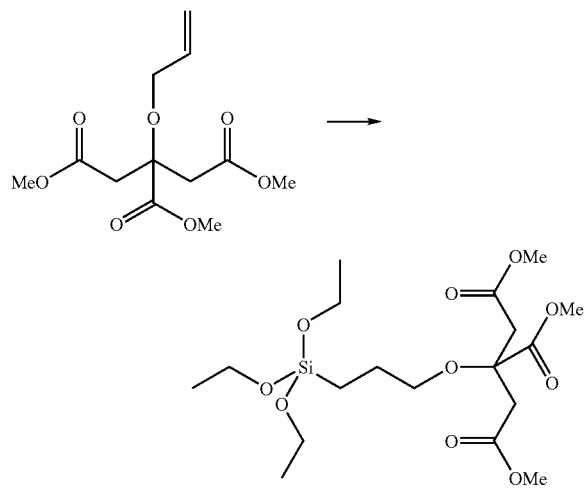

The general procedure as described in Example 2(iii) was followed. $^1$H NMR (CDCl$_3$, 200 MHz): δ 0.51 (m, 2H); 1.13 (t, 9H, J=7.0 Hz); 1.53 (m, 2H); 3.00 (dd, 4H, J$^1$=15.7 Hz, J$^2$=36.5 Hz); 3.30 (t, 2H, J=6.6 Hz); 3.59 (s, 6H); 3.68 (s, 3H); 3.72 (q, 6H, J=7.0 Hz). $^{13}$C NMR (CDCl$_3$, 200 MHz): δ 6.98; 18.89; 23.87; 39.46; 52.34; 53.09; 58.94; 67.39; 78.91; 170.99; 171.85. MS: ES-positive mode: (m/z) (M+H$^+$), calculated: M$^+$=438.55.

Example 7

General Procedure for the Catalytic Hydrogenations

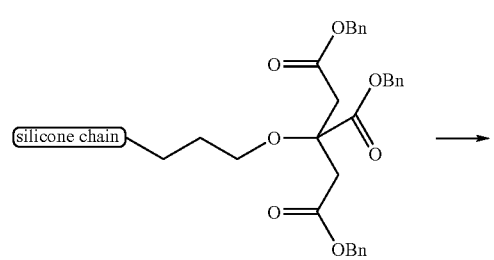

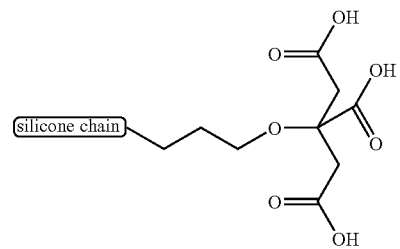

The benzyl-protected silicone-surfactants were dissolved in THF/MeOH (9:1, typically 25 mL per gram). Then, a 5% molar amount of 10% Pd/C was added and hydrogen was bubbled into the mixture under stirring at room temperature. Completion of the reaction was checked by TLC and $^1$H NMR, following the disappearance of the benzylic protons. After completion, the catalyst was removed by filtration over a 0.45 μm Teflon filter. Activated carbon was added to the filtrate and the mixture was stirred for 3 hours before being filtered again. The volatiles were removed in vacuo without heating to afford the corresponding silicone-carboxylic acid surfactants in a quantitative or almost quantitative yield.

(i) Si-1

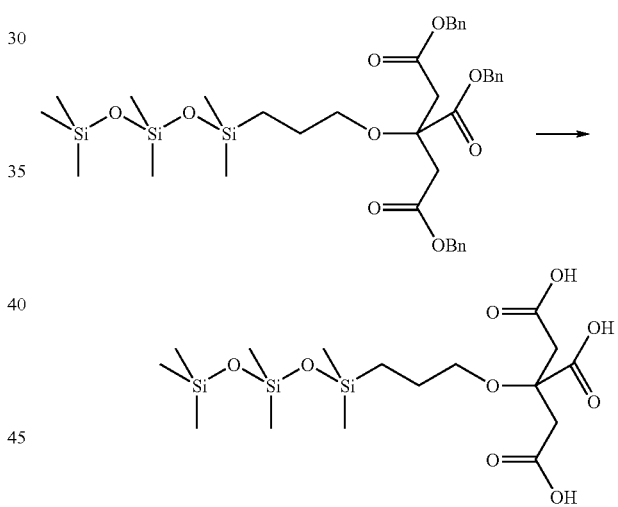

$^1$H NMR (CDCl$_3$, 200 MHz): δ 0.02 (s, 6H); 0.07 (s, 6H); 0.09 (s, 9H); 0.54 (m, 2H); 1.58 (m, 2H); 3.05 (dd, 4H, J$^1$=15.8 Hz, J$^2$=32.0 Hz); 3.45 (t, 2H, J=6.8 Hz). $^{13}$C NMR (CDCl$_3$, 200 MHz): δ −1.81; 0.75; 1.26; 14.34; 24.14; 38.98; 67.25; 78.65; 172.88; 173.47. MS: ES-positive mode: (m/z): 472.1 (M+NH$_4^+$), calculated: M$^+$=454.70.

(ii) Si-5

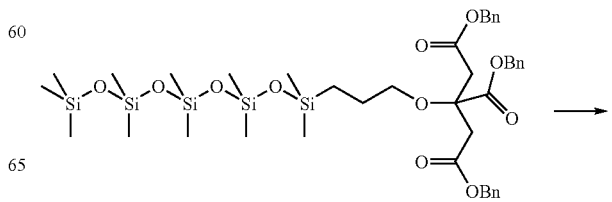

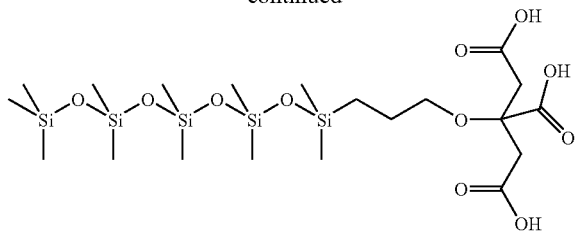
¹H NMR (CD₃OD, 200 MHz): δ 0.08 (m, 33H); 0.53 (m, 2H); 1.58 (m, 2H); 3.05 (dd, 4H, J¹=15.9 Hz, J²=32.1 Hz); 3.45 (t, 2H, J=6.7 Hz). ¹³C NMR (CD₃OD, 200 MHz): δ −0.37; 0.72; 1.26; 14.34; 24.14; 38.96; 67.24; 78.64; 172.87. MS: ES-positive mode: (m/z) 603.3 (M+H⁺), calculated: M⁺=603.01. ES-negative mode: (m/z) 601.2 (M−H⁺), (calculated: M⁺=603.01).
(iii) Si—C18
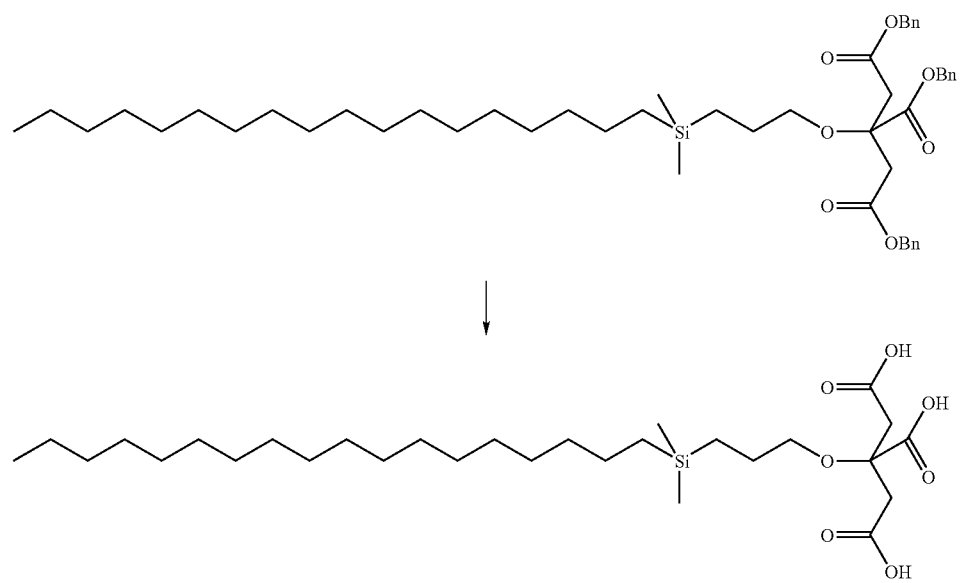
¹H NMR (CD₃OD, 200 MHz): δ −0.04 (s, 6H); 0.49 (m, 4H); 0.89 (t, 3H, J=6.4 Hz); 1.28 (br.s, 32H); 1.51 (m, 2H); 3.05 (dd, 4H, J¹=15.8 Hz, J²=31.6 Hz); 3.44 (t, 2H, J=6.8 Hz). ¹³C NMR (CD₃OD, 200 MHz): δ −4.04; 11.22; 13.76; 15.39; 23.06; 24.29; 24.73; 29.77; 30.08; 32.39; 34.13; 39.06; 67.46; 78.65; 172.88; MS: ES-negative mode: (m/z) 543.6 (M−H⁺), calculated: M⁺=544.85.
(iv) Bola
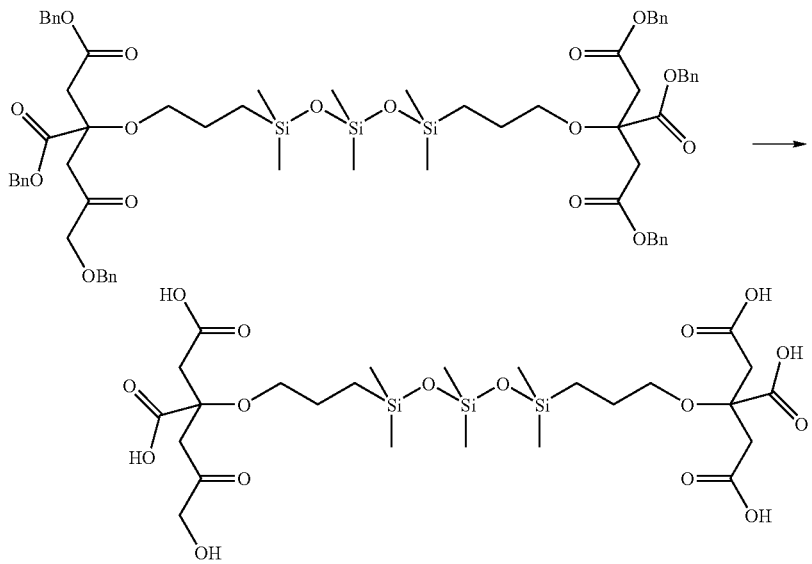

Bola benzyl ester from Example 5 was dissolved in THF/MeOH (9:1, typically 25 mL per gram). Then, a 5% molar amount of 10% Pd/C was added and hydrogen was bubbled into the mixture under stirring at room temperature. Completion of the reaction was checked by TLC and $^1$H NMR, following the disappearance of the benzylic protons. After completion, the catalyst was removed by filtration over a 0.45 µm Teflon filter. Activated carbon was added to the filtrate and the mixture was stirred for more than 3 hours before being filtered again. The volatiles were removed in vacuo without heating to afford Bola in a quantitive or almost quantitative yield. $^1$H NMR (CD$_3$OD, 200 MHz): δ 0.02 (s, 6H); 0.07 (s, 12H); 0.54 (m, 4H); 1.57 (m, 4H); 3.06 (dd, 8H, J$^1$=15.8 Hz, J$^2$=31.6 Hz); 3.45 (t, 4H, J=6.8 Hz). $^{13}$C NMR (CD$_3$OD, 200 MHz): δ −0.35; 0.79; 14.35; 24.15; 39.01; 67.26; 78.66; 172.89; 173.50. MS: ES-positive mode: (m/z) 673.2 (M+H$^+$), calculated: M$^+$=672.87.

Example 8

Properties of the Chelating Silicon-Based Polymer

The silicon-based polymers of the present invention have very low critical micelle concentrations (cmc) and low solubility in water, thus facilitating their structure in aqueous solutions. The critical micelle concentrations data of Si-5 is shown in FIG. 1.

Example 9

Preparation of Metal Nanostructures

As will be described in greater detail hereinafter, silicon-based surfactants containing citrates are able to assemble into a wide variety of morphologies in aqueous solutions. Once assembled, the surfactants can either directly mediate metal ion reduction or maintain their structure while external reducing agents reduce metal cations to metals. Depending on the specific conditions and formulations, different metal structures are possible. For example, the presence of light, changes in pH or the concentrations of surfactant can influence the rate of the metal assembly processes and the ultimate structures that result. The procedure described below relate to the synthesis of gold nanostructures although other metal nanostructures may be prepared in a similar manner.
(i) Bola Amphiphile Templated Synthesis of Gold Nanostructures
The synthesis of the metal nanostructures first involves the preparation of aqueous solutions of Bola amphiphile (Example 7(iv)), typically 50 mL of 2.5 mM stock solutions. These stock solutions were always used immediately after preparation.
a) General Procedure for the Bola Amphiphile Templated Synthesis of Gold Nanoplates without the Use of an External Reducing Agent
An aqueous solution of sodium tetrachloroaurate (2 mL, 2.5 mM, 5×10$^{-3}$ mmol) was added to 2 mL of an aqueous solution of bola amphiphile (Example 7(iv)) (pH=7.80; 2.5 mM; 5×10$^{-3}$ mmol) in a glass scintillation vial. Water (2 mL) was then added and the resulting mixture was left at room temperature without stirring over an aluminium foil-coated shelf at about 2 meters under a conventional neon tube (white light). The mixture was observed to undergo a series of colour changes, from pale yellow initially, to colorless, to green, and finally to light purple pink as the gold nanocrystals slowly settle down. A reaction time of 24 to 28 hours was usually allowed before imaging the products of the reaction.

Changes in the reaction parameters include:
pH of the starting bola amphiphile solution;
ratio between gold cations and bola amphiphile (by changing the volume of each solution mixed);
total concentration of gold and bola amphiphile (2 mL water added, or no water added, or more water added);
exposition of the sample to light (bench top conditions) or in the absence of light (in that case, vials were double-wrapped in aluminium foil to prevent any expositions); and
reaction time.
b) General Procedure for the Bola Amphiphile Templated Synthesis of Gold Nanofoams with the Use of an External Reducing Agent
An aqueous hydrogen tetrachloroaurate solution (1 mL; 2.5 mM; 2.5×10$^{-3}$ mmol) was added to 1 mL of an aqueous solution of bola amphiphile (Example 7(iv)) (pH=8.00; 2.5 mM; 2.5×10$^{-3}$ mmol) in a glass scintillation vial. Water (4 mL) was added and the resulting mixture was vigorously stirred at room temperature. Then, 0.6 mL of a freshly prepared ice-cold aqueous NaBH$_4$ solution (0.1 M) was added and the reaction was stirred for 2 hours. Stirring was stopped and the mixture was aged overnight before imaging. The mixture was observed to undergo a series of colour changes, from pale yellow initially, to orange, to purple and then to brownish purple. The gold foamed slowly or rapidly precipitated from the solution, according to the procedure used.
c) Imaging of the Metal Nanostructures
For TEM, gold nanocrystals were re-dispersed by shaking for a few seconds. Then, a 4 µL drop was deposited over a formvar coated TEM grid and the excess solution was blotted with a Kimwipe paper. The resulting thin film was dried under ambient conditions before imaging.

Figure 6:
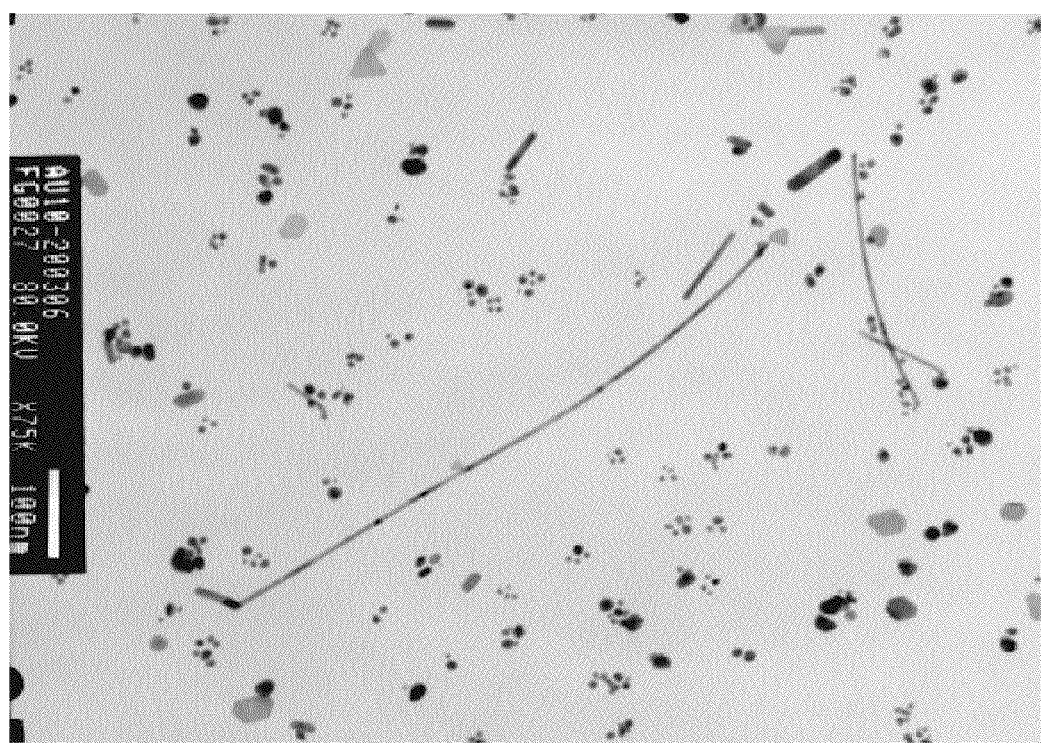
FIG. 6 shows the effect of irradiation with UV light on gold nanostructure formation.
Figure 7:
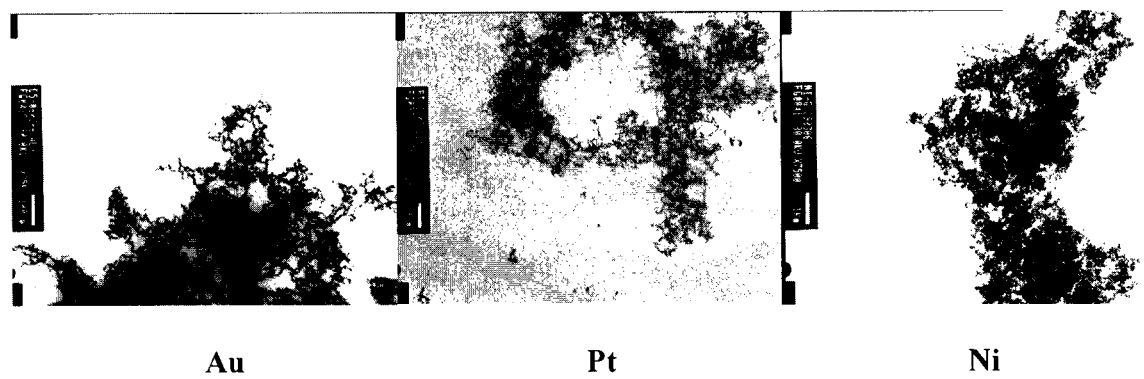
FIG. 7 shows the effect of an external reducing agent on gold nanostructure formation.
Figure 8:
FIG. 8 shows the change in the morphology of the gold nanostructures over time.
Figure 8:
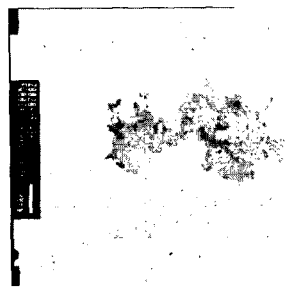
Figure 8:
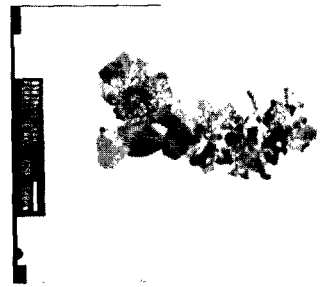

For SEM analysis, the nanocrystals were centrifuged for 30 minutes at 4000 rpm. The colorless supernatant was then removed and the crystals were dispersed in pure water. The centrifugation step was repeated; the supernatant was removed; and the crystals were air-dried. Subsequently, the crystals were applied over a carbon-taped SEM stub for imaging.
d) Modification of the Metal Morphology
(i) UV Irradiation
When the mixture of bola amphiphile (Example 7(iv)) (2 mL; pH=7.40; 2.5 mM) and HAuCl$_4$ (2 mL of 2.5 mM; +2 mL water) was irradiated with intense UV light (centered around 254 nm) for 42 hours, a wide range of gold metal morphologies were observed (FIG. 6). These reactions occurred rapidly and, once irradiation stopped, no further change was observed to the structures.
(ii) External Reducing Agent
The use of a mixture of an aqueous solution of the silicone citrate surfactant (Example 7(iv)) (1 mL; pH=8.00; 2.5 mM; 2.5×10$^{-3}$ mmol) and HAuCl$_4$ (1 mL of 2.5 mM; 2.5×10$^{-3}$ mmol+4 mL water) with NaBH$_4$ as reducing agent (0.6 mL of a 0.1 M solution) led to rapid formation of a nanofoam. As can be seen from FIG. 7, highly dispersed, connected wires were formed from these systems. Analogous reactions with H$_2$PtCl$_6$ (1 mL of 2.5 mM H$_2$PtCl$_6$+1 mL of 2.5 mM bola amphiphile+8 mL H$_2$O+0.6 mL of 0.1 M NaBH$_4$) and NiCl$_2$ (4 mL of 5 mM NiCl$_2$+1 mL of 3 mM bola amphiphile+0.2 mL of 0.1 M NaBH$_4$) lead to the analogous metal structures.
(iii) Structural Evolution
Under less vigorous conditions, it was found that more subtle control was available. At lower concentrations and in the dark, at early stages of the reaction, connected gold wires were observed to form from solutions of (Example 7(iv)) (1.0 mL, 2.5 mM at pH 7.8) and HAuCl$_4$ (1 mL, 2.5 mM+4 mL water). Over time, the complexity of the structure was found to increase with fractal growth of leaf-like morphologies (FIG. 8). Eventually, these leaf-like structures evolved into domains of flat, crystalline gold plates that ultimately developed into triangular/hexagonal plate structures (FIG. 4).

(iv) pH Effects

Figure 9:
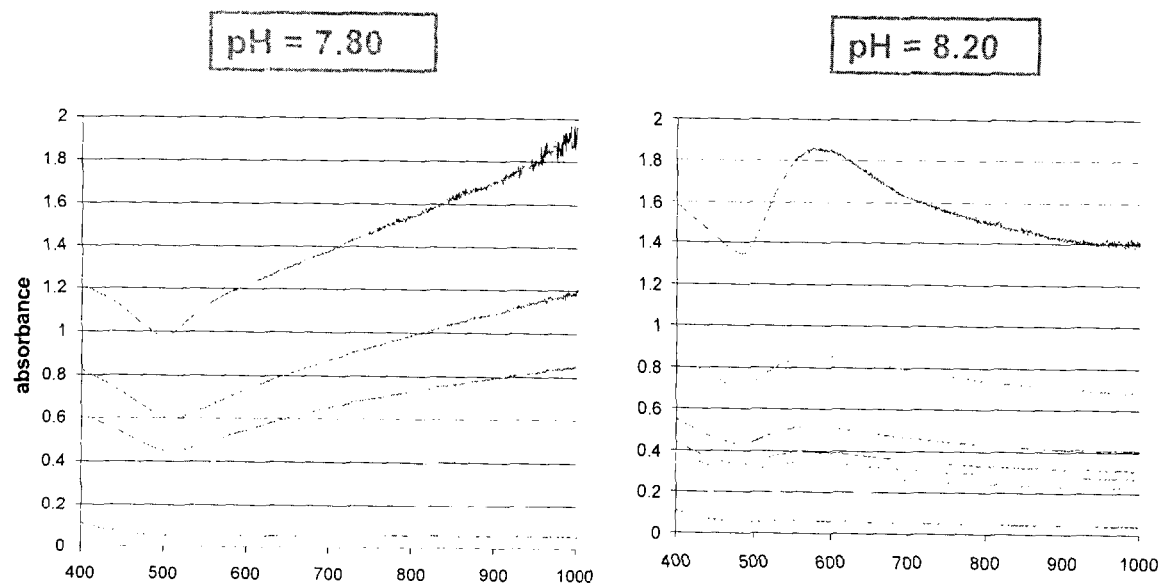
FIG. 9 shows the effect of changes in pH on gold nanostructure formation.
Figure 9:

The maturation of the gold surfaces was found to be highly dependent on pH (2 mL 2.5 mM $HAuCl_4$+2 mL 2.5 mM of bola amphiphile, pH 6.3 or 7.8 or 8.2+2 mL water). For example, at pH 7.8, the reaction operated much more readily than at the only slightly more basic pH of 8.2. As can be seen from the UV plots of FIG. 9, the evolution of gold plates was observed in 8 hours at pH 7.8, whereas large gold plates were not yet developed at pH 8.2.

(v) Presence of Light

Figure 10:
FIG. 10 shows the effect of the presence of light on the rate of conversion of gold ions into gold metal.
Figure 10:

At a given pH (e.g., pH 7.8), the rate of conversion of gold ions into gold metal structures was also found to be dependent on light. Similar structures to those shown from reactions in the dark (FIG. 10) were observed in the presence of ambient light (fluorescent internal light) but the amount of gold metal formed was higher in the same period of time. Thus, the rate of formation of gold metal under these conditions was found to benefit from the presence of light.

(e) Surface Interactions of the Surfactant

Figure 5:
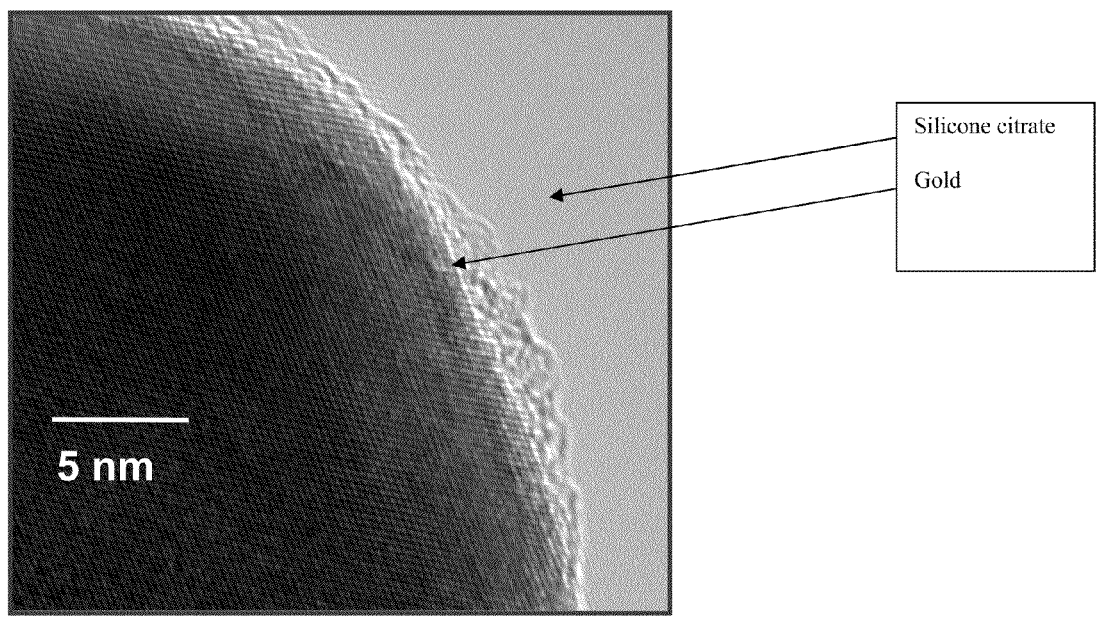
FIG. 5 shows High Resolution Transmission Electronic Microscopy (HRTEM) of the samples from FIG. 4.

The silicon-based surfactant was observed at the interface of the evolving metal surface (FIG. 5). While not wishing to be limited by theory, this supports the contention that interfacial control by the surfactant is associated with the rates of metal evolution and the ultimate morphologies observed.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

What is claimed is:

1. A silicon-based polymer comprising a hydrophobic backbone and having at least one tridentate citrate-based metal binding site X defined as:

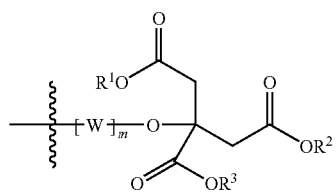

wherein
X is optionally bonded to a metal;
W is a linker group;
m is 0 or 1; and
$R^1$, $R^2$ and $R^3$ are independently selected from the group consisting of H, $C_{1-20}$alkyl, aryl, functional $C_{1-20}$alkyl and functional aryl.

2. The silicon-based polymer according to claim 1, wherein the hydrophobic backbone is selected from the group consisting of a polysiloxane, a polycarbosiloxane, a polysilane and a polycarbosilane.

3. The silicon-based polymer according to claim 2, wherein the linker group W is more stable to hydrolysis than the siloxane linkage in the hydrophobic backbone.

4. The silicon-based polymer according to claim 1, wherein W is selected from the group consisting of $C_{1-20}$alkylene, arylene, functional $C_{1-20}$alkylene and functional arylene.

5. The silicon-based polymer according to claim 1, wherein W is

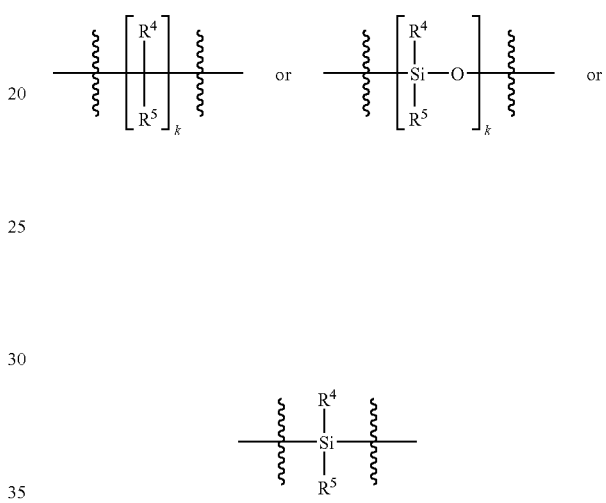

in which k is 1 to 22 and $R^4$ and $R^5$ are independently selected from the group consisting of H, $C_{1-20}$alkyl, aryl, functional $C_{1-20}$alkyl and functional aryl.

6. The silicon-based polymer according to claim 5, wherein k is 1 to 6 and $R^4$ and $R^5$ are independently selected from the group consisting of H, $C_{1-6}$alkyl, aryl, functional $C_{1-6}$alkyl and functional aryl.

7. The silicon-based polymer according to claim 1, wherein m is 1.

8. The silicon-based polymer according to claim 1, wherein $R^1$, $R^2$ and $R^3$ are independently selected from the group consisting of H, $C_{1-6}$alkyl, aryl, functional $C_{1-6}$alkyl and functional aryl.

9. The silicon-based polymer according to claim 1, wherein the metal is selected from the group consisting of alkali metals, alkaline earth metals, Group 13 elements, transition metals, lanthanides and actinides.

10. The silicon-based polymer according claim 1, wherein the metal is a metal ion selected fromgroup consisting of $Ca^{2+}$, $Mg^{2+}$, $Ni^{2+}$, $Fe^{3+}$, $Cu^{2+}$, $Co^{2+}$, $Ag^+$, $Pt^{4+}$, $Pd^{2+}$, $Pd^{4+}$ and $Au^+$.

11. The silicon-based polymer according to claim 1, wherein the metal bonded silicon-based polymer is reduceable to form nanostructures.

12. The silicon-based polymer according to claim 11, wherein the morphology of the nanostructure is dependent on the identity of the silicon-based polymer.

13. The silicon-based polymer according to claim 12, wherein the nanostructure is selected from the group consisting of nanoparticles and agglomerated nanoparticles, agglomerated micelles, reverse micelles, vesicles, sheet structures and wire structures, the latter 5 all containing nanoparticles.

14. A silicon-based polymer of the formula (I):

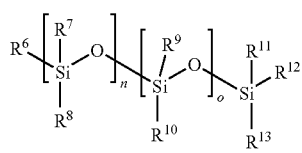
(I)

wherein at least one of $R^6$ to $R^{13}$ is a tridentate citrate-based metal binding site X defined as:

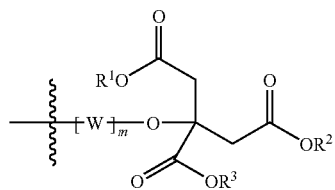

and the remaining $R^6$ to $R^{13}$ are independently selected from the group consisting of H, $C_{1-20}$alkyl, aryl, functional $C_{1-20}$alkyl and functional aryl;
X is optionally bonded to a metal;
$R^1$ to $R^3$ are independently selected from the group consisting of H, $C_{1-20}$alkyl, aryl, functional $C_{1-20}$alkyl and functional aryl;
W is a linker group;
m is 0 or 1;
n and o are each greater than or equal to 0 with the proviso that sum of n and o is greater than 0; and
with the proviso that the silicon-based polymer has a total molecular weight between about 500 and 500,000 g/mol.

15. The silicon-based polymer according to claim 14, wherein the silicon-based polymer has a total molecular weight between about 500 and 15,000 g/mol.

16. The silicon-based polymer according to claim 14, wherein at least one of $R^6$ to $R^{13}$ is a tridentate citrate-based metal binding site X and the remaining $R^6$ to $R^{13}$ are independently selected from the group consisting of H, $C_{1-8}$alkyl, aryl, functional $C_{1-8}$alkyl and functional aryl.

17. The silicon-based polymer according to claim 14, wherein each of $R^6$ and $R^{12}$ is a tridentate citrate-based metal binding site X.

18. The silicon-based polymer according to claim 14, wherein $R^6$ is a tridentate citrate-based metal binding site X.

19. The silicon-based polymer according to claim 14, wherein $R^{12}$ is a tridentate citrate-based metal binding site X.

20. The silicon-based polymer according to claim 14, wherein $R^7$ is a tridentate citrate-based metal binding site X.

21. The silicon-based polymer according to claim 14, wherein $R^1$ to $R^3$ are independently selected from the group consisting of H, $C_{1-8}$alkyl, aryl, functional $C_{1-8}$alkyl and functional aryl.

22. The silicon-based polymer according to claim 14, wherein W is selected from the group consisting of $C_{1-20}$alkylene, arylene, functional $C_{1-20}$alkylene and functional arylene.

23. The silicon-based polymer according to claim 14, wherein W is

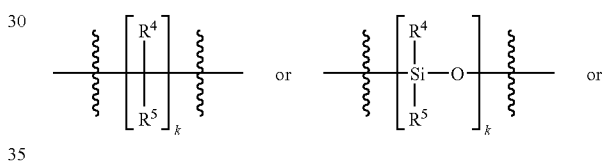

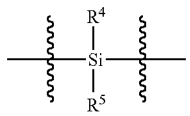

in which k is 1 to 22 and $R^4$ and $R^5$ are independently selected from the group consisting of H, $C_{1-20}$alkyl, aryl, functional $C_{1-20}$alkyl and functional aryl.

24. The silicon-based polymer according to claim 23, wherein k is 1 to 6 and $R^4$ and $R^5$ are independently selected from the group consisting of H, $C_{1-6}$alkyl, aryl, functional $C_{1-6}$alkyl and functional aryl.

25. The silicon-based polymer according to claim 14, wherein m is 1.

26. The silicon-based polymer according to claim 14, wherein sum of n and o is 1 to 10.

27. The silicon-based polymer according to claim 26, wherein sum of n and o is 2 to 6.

28. The silicon-based polymer according to claim 14 that is selected from:
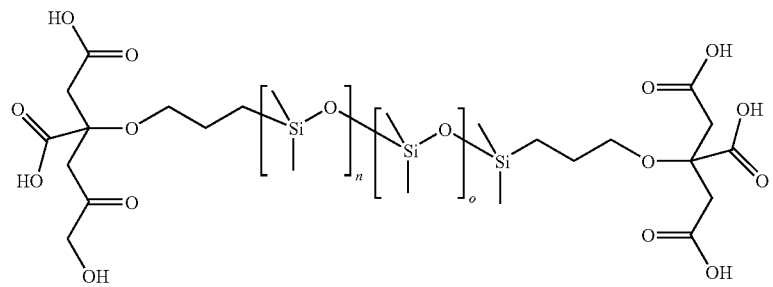
wherein n is 1 and wherein o is greater than or equal to 0;
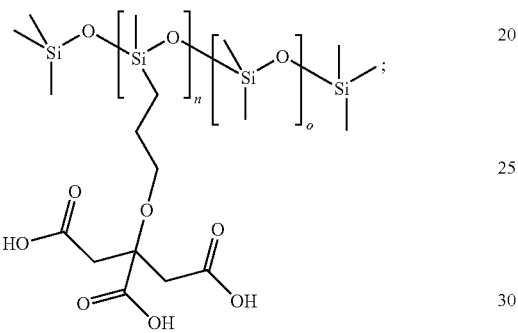
wherein n is greater than or equal to 1 and wherein o is greater than or equal to 0;
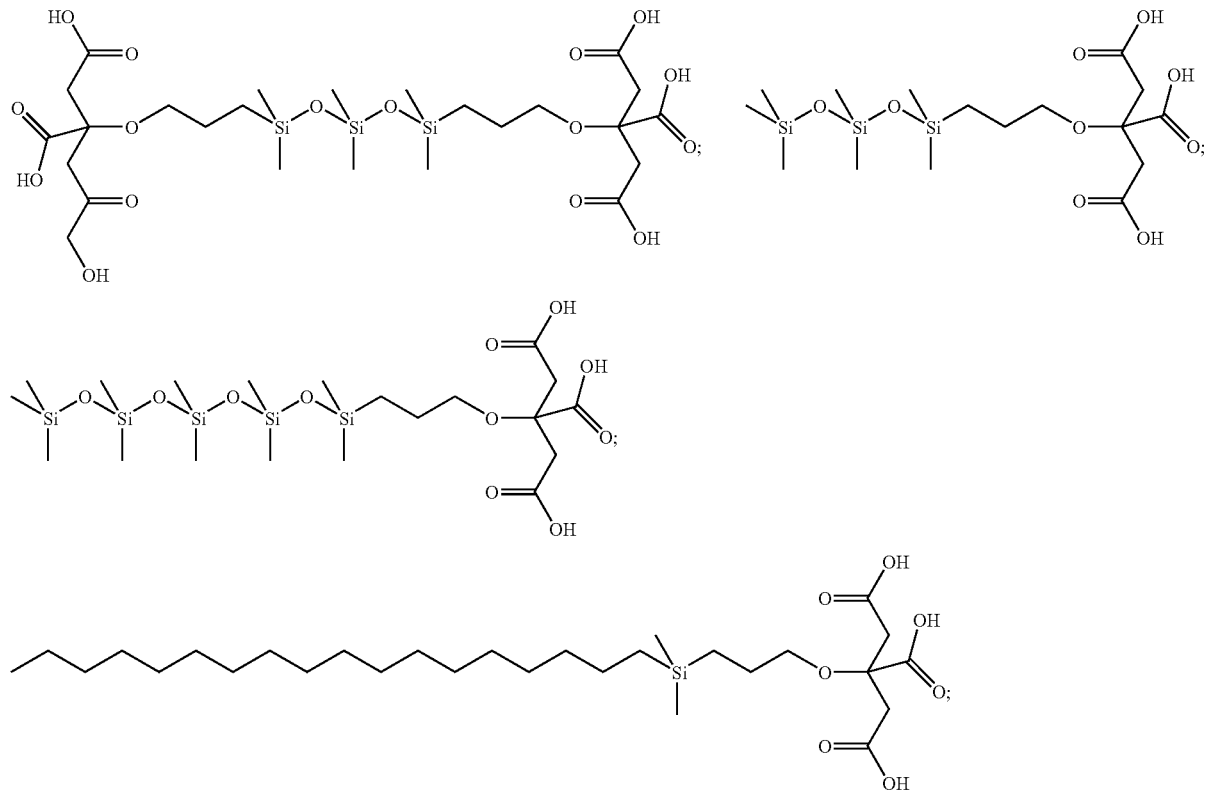

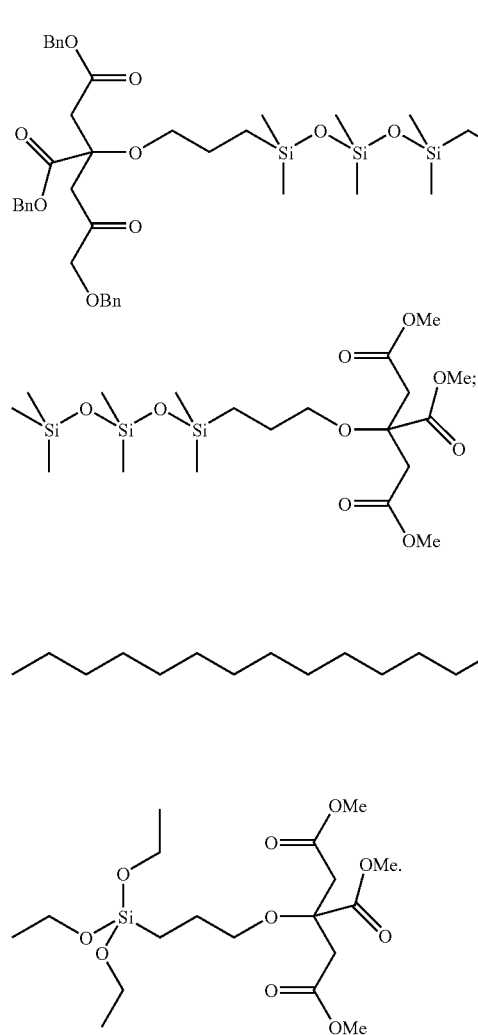
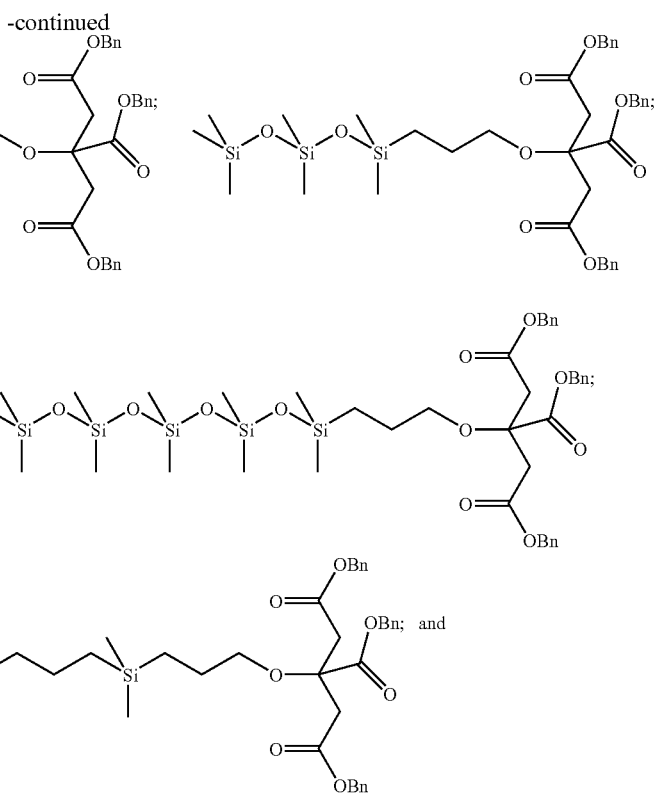

29. The silicon-based polymer according to claim 14, wherein the metal is selected from the group consisting of alkali metals, alkaline earth metals, Group 13 elements, transition metals, lanthanides and actinides.

30. The silicon-based polymer according to claim 14, wherein the metal is a metal ion selected from the group consisting of $Ca^{2+}$, $Mg^{2+}$, $Ni^{2+}$, $Fe^{3+}$, $Cu^{2+}$, $Co^{2+}$, $Ag^+$, $Pt^{4+}$, $Pd^{2+}$, $Pd^{4+}$ and $Au^+$.

31. The silicon-based polymer according to claim 14, wherein the metal bonded silicon-based polymer is reduceable to form nanostructures.

32. The silicon-based polymer according to claim 31, wherein morphology of the nanostructure is dependent on the identity of the silicon-based polymer.

33. The silicon-based polymer according to claim 32, wherein the nanostructure is selected from the group consisting of nanoparticles and agglomerated nanoparticles, agglomerated micelles, reverse micelles, vesicles, sheet structures and wire structures, the latter 5 all containing nanoparticles.

34. A method of preparing metal nanostructures having predetermined morphology comprising:
(a) reacting an aqueous solution of a metal salt with the silicon-based polymer according to claim 1; and
(b) controlling step (a) by making an adjustment selected from the group consisting of altering pH of the aqueous solution, altering nature of light to which the aqueous solution of the metal salt and the silicon-based polymer are exposed, altering nature of the metal ions in the aqueous solution of the metal salt, altering concentration of metal ions in the aqueous solution of the metal salt, altering composition of the silicon-based polymer, altering concentration of the silicon-based polymer and adding reducing agents and combinations thereof.

35. The method according to claim 34, wherein the nature of light is visible light or UV light.

36. The method according to claim 34, wherein the reducing agent is $NaBH_4$.

37. The method according to claim 34, wherein the reducing agent is water soluble or water dispersible.

38. The method according to claim 37, wherein the reducing agent is water soluble or water dispersible borane.

39. The method according to claim 34, wherein step (a) is controlled by altering the pH of the aqueous solution.

* * * * *